United States Patent
Ambati et al.

(10) Patent No.: US 10,562,974 B2
(45) Date of Patent: Feb. 18, 2020

(54) METHODS OF ADMINISTERING IGG1 ANTIBODIES AND METHODS OF SUPPRESSING ANGIOGENESIS

(71) Applicant: University of Kentucky Research Foundation, Lexington, KY (US)

(72) Inventors: Jayakrishna Ambati, Lexington, KY (US); Sandro De Falco, Naples (IT)

(73) Assignee: University of Kentucky Research Foundation, Lexington, KY (US)

( * ) Notice: Subject to any disclaimer, the term of this patent is extended or adjusted under 35 U.S.C. 154(b) by 333 days.

(21) Appl. No.: 14/772,243

(22) PCT Filed: Mar. 13, 2014

(86) PCT No.: PCT/US2014/026340
§ 371 (c)(1),
(2) Date: Sep. 2, 2015

(87) PCT Pub. No.: WO2014/160336
PCT Pub. Date: Oct. 2, 2014

(65) Prior Publication Data
US 2016/0009810 A1    Jan. 14, 2016

Related U.S. Application Data

(60) Provisional application No. 61/780,105, filed on Mar. 13, 2013.

(51) Int. Cl.
| | | |
|---|---|---|
| *A61K 39/39* | (2006.01) | |
| *C07K 16/28* | (2006.01) | |
| *C07K 16/10* | (2006.01) | |
| *C07K 16/22* | (2006.01) | |
| *C07K 16/42* | (2006.01) | |
| *C07K 16/06* | (2006.01) | |
| *C07K 16/24* | (2006.01) | |
| *A61K 39/395* | (2006.01) | |
| *A61K 39/42* | (2006.01) | |
| *A61K 45/06* | (2006.01) | |
| *A61K 39/00* | (2006.01) | |

(52) U.S. Cl.
CPC ...... *C07K 16/2893* (2013.01); *A61K 39/3955* (2013.01); *A61K 39/39566* (2013.01); *A61K 39/42* (2013.01); *A61K 45/06* (2013.01); *C07K 16/06* (2013.01); *C07K 16/1027* (2013.01); *C07K 16/22* (2013.01); *C07K 16/241* (2013.01); *C07K 16/2866* (2013.01); *C07K 16/2887* (2013.01); *C07K 16/4291* (2013.01); *A61K 2039/505* (2013.01); *A61K 2039/507* (2013.01); *C07K 2317/24* (2013.01); *C07K 2317/33* (2013.01); *C07K 2317/52* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 5,567,440 A | * | 10/1996 | Hubbell | ............... A61K 9/5031 424/484 |
| 2007/0191273 A1 | * | 8/2007 | Ambati | ............... A61K 38/177 514/44 R |
| 2009/0214541 A1 | | 8/2009 | Gillies et al. | |
| 2011/0008322 A1 | | 1/2011 | Zauderer et al. | |
| 2011/0311554 A1 | | 12/2011 | Gomer et al. | |
| 2013/0266587 A1 | * | 10/2013 | Pitzalis | .................. C07K 16/28 424/172.1 |

FOREIGN PATENT DOCUMENTS

| | | | | |
|---|---|---|---|---|
| CN | 1793179 | * | 6/2006 | |
| EP | 2174667 A1 | * | 4/2010 | ............. A61K 31/00 |
| WO | WO-2012064627 A2 | * | 5/2012 | ............. A61K 38/47 |
| WO | WO -2014074905 A1 | * | 5/2014 | ........... C07K 16/248 |

OTHER PUBLICATIONS

Avery et al. Intravitreal Bevacizumab (Avastin) for Neovascular Age-Related Macular Degeneration Ophthalmology, vol. 113, Issue 3, Mar. 2006, pp. 363-372.e5. (Year: 2006).*
ClinicalTrials.gove archive NCT01543568. AflibercepT for Subjects Who Are Incomplete Responders to mUltiple Intravitreal Injections of Ranibizumab, Anti-VegF (The TURF Study). pp. 1-5. Mar. 2, 2012 (Year: 2012).*
Yoshimura et al. Involvement of Th17 cells and the effect of anti-IL-6 therapy in autoimmune uveitis. Rheumatology 2009;48:347-354. (Year: 2009).*
Iwanami et al. Crucial Role of the Interleukin-6/Interleukin-17 Cytokine Axis in the Induction of Arthritis by Glucose-6-Phosphate Isomerase. Arthritis & Rheumatism vol. 58, No. 3, Mar. 2008, pp. 754-763. (Year: 2008).*
Rosenfeld et al. Ranibizumab for Neovascular Age-Related Macular Degeneration(N Engl J Med 2006; 355:1419-1431) (Year: 2006 ).*
Shinriki et al Humanized Anti-Interleukin-6 Receptor Antibody Suppresses Tumor Angiogenesis and In vivo Growth of Human Oral Squamous Cell Carcinoma. (Clin Cancer Res 2009;15(17):5426-34). (Year: 2009).*
Qazi et al. Mediators of ocular angiogenesis. J Genet. Dec. 2009 ; 88(4): 495-515. (Year: 2009).*
Nowak et al. A prospective . . . for the treatment of choroidal neovascularization. The efficacy of verteporfin photodynamic therapy, intravitreal bevacizumab and transpupillary thermotherapy in patients with neovascular age-related macular degeneration. Med Sci Monit, 2012; 18(6): CR374-380. (Year: 2012).*

(Continued)

*Primary Examiner* — Maher M Haddad
(74) *Attorney, Agent, or Firm* — Stites & Harbison PLLC; Mandy Wilson Decker; Sean P. Ritchie

(57) ABSTRACT

A method of suppressing angiogenesis involves administering to a subject an isolated Fc fragment of an IgG1 antibody, or an IgG1 antibody.

9 Claims, 18 Drawing Sheets

(56) References Cited

OTHER PUBLICATIONS

Kim et al. FcRn receptor-mediated pharmacokinetics of therapeutic IgG in the eye. Molecular Vision 2009; 15:2803-2812 (Year: 2009).*

Izumi-Nagai et al. Interleukin-6 Receptor-Mediated Activation of Signal Transducer and Activator of Transcription-3 (STAT3) Promotes Choroidal Neovascularization. Am J Pathol 2007, 170:2149-2158 (Year: 2007).*

Gaudreault et al. Preclinical Pharmacokinetics of Ranibizumab (rhuFabV2) after a Single Intravitreal Administration. Invest Ophthalmol Vis Sci. 2005;46:726-733 (Year: 2006).*

Sheybani et al (Review of Ophthalmology, Mar. 19, 2010, pp. 1-3) (Year: 2010).*

Sang and Hughes. Triple Therapy (Reduced Duration PDT with Same Day Dexamethasone and Bevacizumab) as Rescue Treatment in Patients with Previously Treated Exudative AMD: One Year Follow-up. Investigative Ophthalmology & Visual Science Apr. 2009, vol. 50, 1927 (Year: 2009).*

Tseng et al. A fusion protein with the receptor-binding domain of vascular endothelial growth factor-A (VEGF-A) is an antagonist of angiogenesis in cancer treatment. Cancer Biology & Therapy, 10:9, 865-873 (Year: 2010).*

Cheung et al. Combined anti-PIGF and anti-VEGF Therapy Ameliorates Pathological Neovascularization and Improves Retinal Revascularization in the Murine Model of Oxygen Induced Ischemic Retinopathy (OIR). ARVO Annual Meeting Abstract Search and Program Planner, (May 2011) vol. 2011, pp. 6064. (Year: 2011).*

Cao et al. Neutralization of Angiopoietin-2 Inhibits Ocular Angiogenesis and Vascular Leak, and Promotes Regression of Choroidal Neovascularization. ARVO Annual Meeting Abstract Search and Program Planner, (May 2011) vol. 2011, pp. 1799. (Year: 2011).*

Lobov et al. The Dll4/Notch Pathway Controls Blood Vessel Remodeling and Regression by Modulating Vasoconstriction and Blood Flow Independently of VEGF-A. IOVS, (Apr. 2010) vol. 51, No. 13, pp. 3334. (Year: 2010).*

Nahta, Rita et al., "The HER-2-targeting antibodies trastuzumab and pertuzumab synergistically inhibit the survival of breast cancer cells," Cancer Research, 2004, vol. 64, No. 7, pp. 2343-2346.

Rahimi, Nader, "A role for protein ubiquitination in VEGFR-2 signalling and angiogenesis," Biochemical Society Transactions, 2009, vol. 37, pp. 1189-1192.

Meyer, R.D. et al., "c-Cb1 inhibits angiogenesis and tumor growth by suppressing activation of PLC?1," Oncogene, 2011, vol. 30, pp. 2198-2206.

Nelson, A. L., Dhimolea, E. & Reichert, J. M. Development trends for human monoclonal antibody therapeutics. Nat Rev Drug Discov 9, 767-774 (2010).

Presta, L. G. et al. Humanization of an anti-vascular endothelial growth factor monoclonal antibody for the therapy of solid tumors and other disorders. Cancer Res 57, 4593-4599 (1997).

Martin, D. F. et al. Ranibizumab and bevacizumab for neovascular age-related macular degeneration. N Engl J Med 364, 1897-1908 (2011).

Yu, L. et al. Interaction between bevacizumab and murine VEGF-A: a reassessment. Invest Ophthalmol Vis Sci 49, 522-527 (2008).

Gerber, H. P. et al. Mice expressing a humanized form of VEGF-A may provide insights into the safety and efficacy of anti-VEGF antibodies. Proc Natl Acad Sci U S A 104, 3478-3483 (2007).

Liang, W. C. et al. Cross-species vascular endothelial growth factor (VEGF)-blocking antibodies completely inhibit the growth of human tumor xenografts and measure the contribution of stromal VEGF. J Biol Chem 281, 951-961 (2006).

Rabinowitz, R., Priel, A., Rosner, M., Pri-Chen, S. & Spierer, A. Avastin treatment reduces retinal neovascularization in a mouse model of retinopathy of prematurity. Curr Eye Res 37, 624-629 (2012).

Manzano, R. P. et al. Inhibition of experimental corneal neovascularisation by bevacizumab (Avastin). Br J Ophthalmol 91, 804-807 (2007).

Avisar, I., Weinberger, D. & Kremer, I. Effect of subconjunctival and intraocular bevacizumab injections on corneal neovascularization in a mouse model. Curr Eye Res 35, 108-115 (2010).

Ravetch, J. V. & Kinet, J. P. Fc receptors. Annu Rev Immunol 9, 457-492 (1991).

Chen, Y. et al. Selection and analysis of an optimized anti-VEGF antibody: crystal structure of an affinity-matured Fab in complex with antigen. J Mol Biol 293, 865-881 (1999).

Tao, M. H. & Morrison, S. L. Studies of aglycosylated chimeric mouse-human IgG. Role of carbohydrate in the structure and effector functions mediated by the human IgG constant region. J Immunol 143, 2595-2601 (1989).

Walker, M. R., Lund, J., Thompson, K. M. & Jefferis, R. Aglycosylation of human IgG1 and IgG3 monoclonal antibodies can eliminate recognition by human cells expressing human Fc gamma RI and/or Fc gamma RII receptors. Biochem J 259, 347-353 (1989).

Marino, M., Ruvo, M., De Falco, S. & Fassina, G. Prevention of systemic lupus erythematosus in MRL/lpr mice by administration of an immunoglobulin-binding peptide. Nat Biotechnol 18, 735-739 (2000).

Nishijima, K. et al. Vascular endothelial growth factor-A is a survival factor for retinal neurons and a critical neuroprotectant during the adaptive response to ischemic injury. Am J Pathol 171, 53-67 (2007).

Saint-Geniez, M. et al. Endogenous VEGF is required for visual function: evidence for a survival role on muller cells and photoreceptors. PLoS One 3, e3554 (2008).

Gelfand, E. W. Intravenous immune globulin in autoimmune and inflammatory diseases. N Engl J Med 367, 2015-2025 (2012).

Rogers, K. A., Scinicariello, F. & Attanasio, R. IgG Fc receptor III homologues in nonhuman primate species: genetic characterization and ligand interactions. J Immunol 177, 3848-3856 (2006).

Smith, P., DiLillo, D. J., Bournazos, S., Li, F. & Ravetch, J. V. Mouse model recapitulating human Fcgamma receptor structural and functional diversity. Proc Natl Acad Sci U S A 109, 6181-6186 (2012).

* cited by examiner

METHODS OF ADMINISTERING IGG1 ANTIBODIES AND METHODS OF SUPPRESSING ANGIOGENESIS

RELATED APPLICATION

This application claims priority from U.S. Provisional Patent Application Ser. No. 61/780,105, which was filed on Mar. 13, 2013, the entire disclosure of which is incorporated herein by this reference.

TECHNICAL FIELD

The presently-disclosed subject matter relates to administration of IgG1 antibodies, and to suppression of angiogenesis using intravenous human immunoglobulin (IVIG), IgG1 antibodies, and/or Fc fragments of same.

INTRODUCTION

Angiogenesis is a process of forming new capillaries as endothelial cells of preexisting blood vessels decompose extracellular matrix, migrate, divide, and differentiate to form new capillaries, which does not occur except in a particular case, such as growth, reproduction, or healing wounds. However, excessive angiogenesis has been reported in diseases such as growth and metastasis of a malignant tumor, age-related macular degeneration, rheumatoid arthritis, diabetic retinopathy, psoriasis, and chronic inflammation.

Formation of blood vessels requires a complicate set of processes including growth, migration, and division of vascular endothelial cells, and formation of capillaries, and many vascular endothelial growth factors and vascular endothelial inhibition factors involved in the set of processes have been discovered. The vascular endothelial inhibition factors are activated against activity of the vascular endothelial growth factors, which are necessary in the formation of blood vessel. Therefore, many anti-angiogenesis products target vascular endothelial growth factor-A (VEGFA, a.k.a. VEGF). Fewer products act to suppress angiogenesis via other targets.

Aberrant angiogenesis is implicated in a variety of diseases that collectively affect nearly 10% of the world's population. Accordingly, there remains a need in the art for unique angiogenesis suppressors and new approaches for suppressing angiogenesis to facilitate the treatment of such diseases.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

A commonly-used anti-angiogenic drug is bevacizumab, a humanized IgG1 monoclonal antibody that targets vascular endothelial growth factor-A (VEGFA, a.k.a. VEGF) and is approved for various cancers and widely used in age-related macular degeneration. Bevacizumab had been thought to inhibit angiogenesis by targeting human VEGFA; however, it was reported to inhibit angiogenesis in mouse models[8-14], even though bevacizumab does not target mouse VEGFA and is specific for human VEGFA.

The present inventor surprisingly discovered that bevacizumab acts to suppress angiogenesis not only via its target, VEGFA, but rather also via activation of FcγRI via its Fc fragment (FcγRI is also known as CD64). The present inventor surprisingly discovered that bevacizumab's anti-angiogenic activity occurs not only because it is designed to target a particular protein, but also because it includes an Fc fragment that is capable of activating FcγRI.

In this regard, as disclosed herein, any IgG1 antibody including an Fc fragment, intravenous human immunoglobulin (IVIG), and/or isolated Fc fragment can be used to suppress angiogenesis.

Several monoclonal antibody therapies are now approved by the FDA, EMEA, and other regulatory agencies for the treatment of numerous diseases including age-related macular degeneration (AMD), asthma, autoimmune disorders, and various cancers[1]. In addition, there are hundreds of monoclonal antibodies under evaluation in thousands of clinical trials. Such antibodies that were not contemplated for use to suppress angiogenesis are proposed herein for a unique use, with the benefit that many of such antibodies have already obtained regulatory approval and/or are undergoing clinical safety assessment.

The presently-disclosed subject matter includes methods of suppressing angiogenesis, which involve administering to a subject in need of suppression of angiogenesis an isolated Fc fragment of an IgG1 antibody, an IgG1 antibody, and/or WIG.

In some instances, IgG1 antibodies can be administered to treat a subject wherein suppression of angiogenesis is contraindicated (including wherein suppression of angiogenesis is not desired). In this regard, the presently-disclosed subject matter also provides for methods of administering IgG antibodies if suppression of angiogenesis in the subject is not contraindicated.

The present inventor has also surprisingly discovered that intravitreous administration of Fc fragment-containing IVIG suppressed choroidal neovascularization as effectively as intravenous administration. Accordingly, the presently-disclosed subject matter further includes methods of suppressing angiogenesis, including intravitreously administering to the subject an isolated Fc fragment of an IgG1 antibody, an IgG1 antibody, and/or IVIG. Screening methods for identifying angiogenesis suppressors are also provided herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
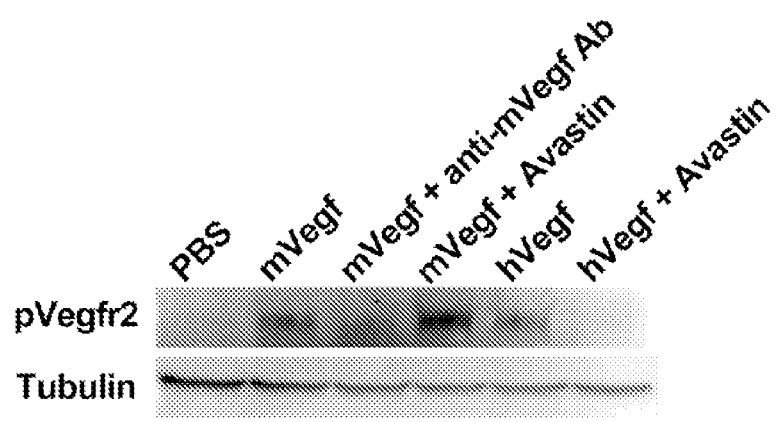
FIG. 1: Avastin does not inhibit mouse VEGF signaling. Western blotting shows that mouse VEGF (mVegf) and human VEGF (hVegf) induce phosphorylation of VEGFR2 (pVegfr2) in mouse Py4 endothelial cells. A neutralizing anti-mouse Vegf antibody reduced mouse VEGF induced VEGF2 phosphorylation but Avastin (a humanized IgG1 antibody that specifically targets human Vegf but not mouse Vegf) did not do so. Avastin did reduce human VEGF induced VEGFR2 phosphorylation. Tubulin blotting shows protein loading.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods of administering an IVIG containing an Fc fragment, an IgG1 antibody contacting an Fc fragment, and/or an isolated Fc fragment. The presently-disclosed subject matter further includes methods of suppressing angiogenesis. The presently-disclosed subject matter further includes methods of screening for angiogenesis suppressors.

With regard to the use of an isolated Fc fragment, it is noted that Fcgr1 has not been previously associated with suppression of angiogenesis in any published report. Moreover, since both Lucentis (an IgG1 Fab fragment) and Avastin (a full-length IgG1 containing both the Fab and Fc fragments) suppress angiogenesis, one of ordinary skill in the art would have surmised that the Fc fragment is unnecessary for anti-angiogenic activity. As such, it is unexpected that the isolated Fc fragment has utility for anti-angiogenic treatment.

Unless otherwise indicated, the term "administering" is inclusive of all means known to those of ordinary skill in the art for providing a pharmaceutical preparation to a subject, administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and subcutaneous administration. Administration can be continuous or intermittent. A preparation can be administered therapeutically; that is, administered to treat an existing condition of interest. A preparation can be administered prophylactically; that is, administered for prevention of a condition of interest.

As used herein, the term "contraindicated" refers to any condition in a patient which renders a particular line of treatment, including the administration of drugs (e.g., an anti-angiogenic agent), undesirable or improper. This condition may be preexisting, or may develop while the patient is taking the drugs, including conditions which may result directly or indirectly from treatment with the drugs. A particular line of treatment, including administration of drugs, may also be considered "contraindicated," as the term is used herein, if use of a drug by subjects who are also taking another drug is known or suspected of producing an adverse side effect in those subjects.

As used herein, "IgG1 antibody" or "IgG1" refer to immunoglobulin G subclass 1, including an Fc region or Fc fragment, i.e., the Fc fragment has not been cleaved from the antibody. Antibodies as used herein include monoclonal, polyclonal, chimeric, single chain, bispecific, simianized, human, and humanized or primatized antibodies. As used herein, "intravenous human immunoglobulin (IVIG)" refers to the blood product, including IgG, including an Fc region or Fc fragment, i.e., the Fc fragment has not been cleaved from the antibody. "Fc region" and "Fc fragment" refer to the Fragment, crystalizable (Fc) region of an IgG1 antibody. The term "isolated" when used in the context of an Fc fragment, is the Fc fragment that exists apart from the remainder of an IgG1 antibody. Use of the term "isolated" in connection with an Fc fragment does not preclude that the Fc fragment may comprise additional amino acids or other elements that are not particularly part of the Fc region; rather, it is simply to clarify that the Fc fragment exists apart from the remainder of the IgG1 antibody.

As used herein, the term "subject" refers to a target of treatment. The subject of the herein disclosed methods can be a vertebrate, such as a mammal, a fish, a bird, a reptile, or an amphibian. Thus, the subject of the herein disclosed methods can be a human or nonhuman. Thus, veterinary therapeutic uses are provided in accordance with the presently disclosed subject matter.

As will be recognized by one of ordinary skill in the art, the terms "suppression," "suppressing," "suppressor," "inhibition," "inhibiting" or "inhibitor" do not refer to a complete elimination of angiogenesis in all cases. Rather, the skilled artisan will understand that the term "suppressing" or "inhibiting" refers to a reduction or decrease in angiogenesis. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

As used herein, the terms "treatment" or "treating" relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

In some embodiments of the presently-disclosed subject matter the method includes identifying a subject in need of treatment with an IgG1 antibody; determining whether suppression of angiogenesis in the subject is contraindicated; and if suppression of angiogenesis in the subject is not contraindicated, administering the IgG1 antibody. In some embodiments, the IgG1 antibody is not selected from the IgG1 antibodies set forth in Table A. In some embodiments, the IgG1 antibody is selected from the IgG1 antibodies set forth in Table B.

In some embodiments of the presently-disclosed subject matter the method includes identifying a subject in need of suppression of angiogenesis; and administering to the subject an isolated Fc fragment of an IgG1 antibody and/or an IgG1 antibody. In some embodiments, the IgG1 antibody is not selected from the IgG1 antibodies set forth in Table A. In some embodiments, the IgG1 antibody is selected from the IgG1 antibodies set forth in Table B.

TABLE A

| | |
|---|---|
| Bevacizumab (Avastin) | Efalizumab (Raptiva) |
| Trastuzumab (Herceptin) | Canakinumab (Ilaris) |
| Ado-trastuzumab emtansine (Kadcyla) | Pertuzumab (Perjeta) |
| Adalimumab (Humira) | Intravenous immunoglobulin (IVIG) |
| Golimumab (Simponi) | |

TABLE B

| | | |
|---|---|---|
| Tocilizumab (Actemra) | ACE-011 | AIN457 |
| Atilizumab (RoActemra) | ACE-031 | CD4-IgG |
| Ofatumumab (Arzerra) | MGAWN1 | J695 |
| Alemtuzumab (Campath) | NCT01736683 | BIIB023 |
| Palivizumab (Synagis) | MNRP1685A | AIN457 |
| Motavizumab (Numax) | IMC-A12 | IMC-1121B |
| Raxibacumab (ABThrax) | IMC 1121B | MEDI4893 |
| Belimumab (Benlysta) | FG-3019 | Nimotuzumab |
| Omalizumab (Xolair) | MT203 | Mepolizumab |
| Ipilmumab (Yervoy) | Necitumumab | TRC105 |
| Daclizumab (Zenapax) | Immunex | solanezumab |
| Ustekinumab (Stelara) | hLL1 | ficlatuzumab |
| Alefacept (Amevive) | IMGN388 | |
| Elotuzumab | AMG 479 | |

In some embodiments of the presently-disclosed subject matter the method includes identifying a subject in need of suppression of angiogenesis; and intravitreously administering to the subject an isolated Fc fragment of an IgG1 antibody, an IgG1 antibody, and/or intravenous human immunoglobulin (IVIG).

Neither WIG nor IgG1 antibodies (apart from Avastin) are formulated for intraocular administration. As such, they are not contemplated for such a mode of delivery. Furthermore, the IgG1 the IgG1 antibodies in Table B are not known to influence previously described pathways of angiogenesis. As such, their use in the eye would not be expected. Nevertheless, the present inventor discovered that Intravitreous administration is surprisingly effective.

Damianovich et al. reports that WIG reduces angiogenesis and attributes it to the presence of anti-VEGF antibodies contained in the IVIG. Therefore, one of ordinary skill in the art would not expect "generic" IgGs not containing anti-VEGF antibodies to suppress angiogenesis. See Damianovich et al. Anti-vascular endothelial growth factor (VEGF) specific activity of intravenous immunoglobulin (IVIg). Int. Immunol. (2009) 21 (9): 1057-1063. Surprisingly, as reported herein, such IgGs that do not contain anti-VEGF antibodies indeed suppress angiogenesis.

The presently-disclosed subject matter includes methods involving administration of a combination of an isolated Fc fragment of an IgG1 antibody, an IgG1 antibody, and/or IVIG; and a drug that is otherwise useful for in the context of suppressing angiogenesis. The presently-disclosed subject matter further includes compositions that include an isolated Fc fragment of an IgG1 antibody, an IgG1 antibody, and/or IVIG; and a drug that is otherwise useful for in the context of suppressing angiogenesis.

In some embodiments of the methods as described herein, the method further involves administering a drug selected from the group consisting of: Avastin, Lucentis, Herceptin, sorafenib (Nexavar), sunitinib (Sutent), pazopanib (Votrient), everolimus (Afinitor).

In some embodiments of the presently-disclosed subject matter, a method of suppressing angiogenesis involves identifying a subject in need of suppression of angiogenesis; and administering to the subject an isolated Fc fragment of an IgG1 antibody, an IgG1 antibody, and/or IVIG; and a drug selected from the group consisting of: Avastin, Lucentis, Herceptin, sorafenib (Nexavar), sunitinib (Sutent), pazopanib (Votrient), everolimus (Afinitor).

In some embodiments of the presently-disclosed subject matter, a method of suppressing angiogenesis involves identifying a subject in need of suppression of angiogenesis; and administering to the subject a pharmaceutical composition, which includes an isolated Fc fragment of an IgG1 antibody, an IgG1 antibody, and/or IVIG; and a drug selected from the group consisting of: Avastin, Lucentis, Herceptin, sorafenib (Nexavar), sunitinib (Sutent), pazopanib (Votrient), everolimus (Afinitor).

The presently-disclosed subject matter further includes a pharmaceutical composition, comprising an isolated Fc fragment of an IgG1 antibody, an IgG1 antibody, and/or IVIG; and a drug selected from the group consisting of: Avastin, Lucentis, Herceptin, sorafenib (Nexavar), sunitinib (Sutent), pazopanib (Votrient), everolimus (Afinitor).

In some embodiments, the composition can further include a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

In some embodiments of the methods described herein, the subject in need of treatment for a condition associated with angiogenesis. Conditions associated with angiogenesis will be known to those of ordinary skill in the art and include, but are not limited to cancer, diabetic blindness, age-related macular degeneration, rheumatoid arthritis, psoriasis, atherosclerosis.

The presently-disclosed subject matter further includes methods of identifying angiogenesis suppressors, including measuring activation of FcγRI and/or c-cbl. In some embodiments, the method of identifying angiogenesis suppressors involves determining the ability of the candidate suppressor to induce phosphorylation of c-cbl in macrophages, endothelial cells, or other cells, e.g., by Western blotting. In some embodiments, the method of identifying angiogenesis suppressors involves determining the ability of the candidate suppressor to bind with FcγRI, e.g., by ELISA or surface plasmon resonance assays.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1: Bevacizumab Inhibits Mouse Corneal Angiogenesis Via FcγRI

Bevacizumab has no detectable binding to mouse Vegfa by surface plasmon resonance and does not block mouse Vegfa-induced retinal capillary endothelial cell proliferation[5-7]. To further verify that bevacizumab does not functionally neutralize mouse Vegfa, its ability to inhibit the activation of the Vegfr2 receptor tyrosine kinase in mouse Py4 hemangioma endothelial cells was tested. As expected, bevacizumab inhibited Vegfr2 phosphorylation induced by human VEGFA but not by mouse Vegfa (FIG. 1). In contrast, an anti-mouse Vegfa neutralizing antibody blocked mouse Vegfa-induced Vegfr2 phosphorylation.

Figure 2:
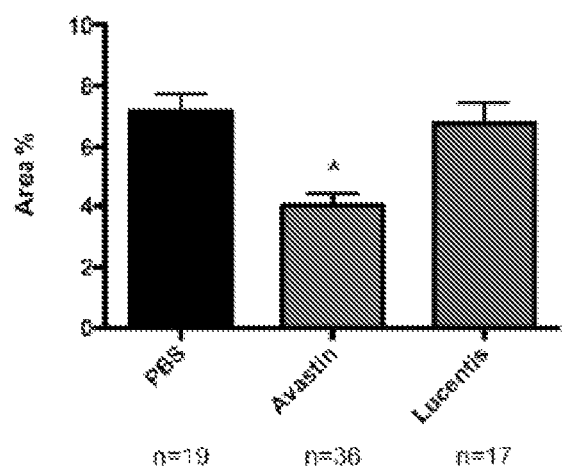
FIG. 2: Lucentis does not inhibit corneal neovascularization. Avastin (a full length humanized IgG1 antibody that specifically targets human VEGF-A but not mouse Vegfa; red), but not Lucentis (a humanized IgG1 Fab antibody fragment that specifically targets human VEGF-A but not mouse Vegfa; gray), reduced corneal hemangiogenesis compared to PBS (black) injection in wild-type mice. * P<0.05.

The effects of bevacizumab were tested in a mouse model of suture-injury-induced corneal angiogenesis that is pathophysiologically relevant to the human condition and is driven in large part by Vegfa[16]. Various drugs were injected into the cornea stroma immediately after surgery and at 4 and 8 days thereafter. By day 10, it was found that bevacizumab inhibited corneal hemangiogenesis in wild-type mice compared to PBS administration (FIG. 2). However, administration of equimolar amounts of ranibizumab, a humanized monoclonal IgG1 Fab fragment that binds human VEGFA but not mouse Vegfa[6,17], did not inhibit corneal hemangiogenesis (FIG. 2). Since bevacizumab and ranibizumab had nonsynonymous effects in this mouse model, it was suspected that the anti-angiogenic action of bevacizumab was due not to Vegfa inhibition but rather due to IgG1 Fc-mediated effects.

Figure 3:
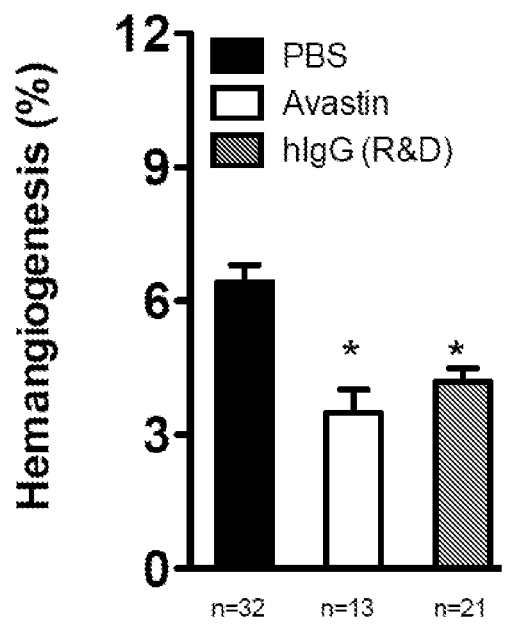
FIG. 3: Avastin and human IgG1 inhibit mouse corneal neovascularization. Intrastromal injection of Avastin reduced corneal hemangiogenesis compared to PBS injection in wild-type mice. Human IgG1 (hIgG) from R&D Systems also reduced corneal hemangiogenesis compared to PBS. * P<0.05.
Figure 4:
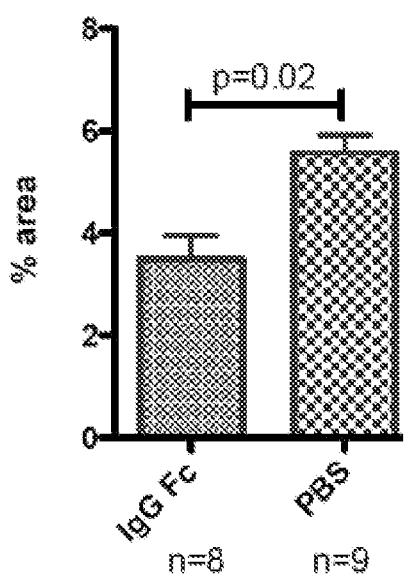
FIG. 4: Fc fragment of human IgG1 inhibits corneal neovascularization. The Fc fragment of human IgG1 reduced corneal hemangiogenesis compared to PBS injection in wild-type mice.
Figure 5:
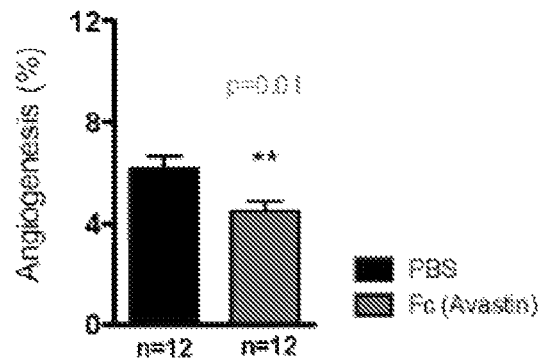
FIG. 5: Fc fragment of Avastin inhibits corneal neovascularization. An enzymatically cleaved Fc fragment of Avastin (red) reduced corneal hemangiogenesis compared to PBS (black) injection in wild-type mice.
Figure 6:
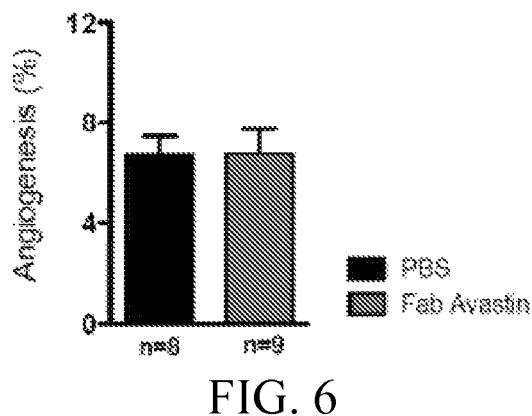
FIG. 6: Fab fragment of Avastin does not inhibit corneal neovascularization. An enzymatically cleaved Fab fragment of Avastin did not reduce corneal hemangiogenesis compared to PBS injection in wild-type mice.
Figure 7:
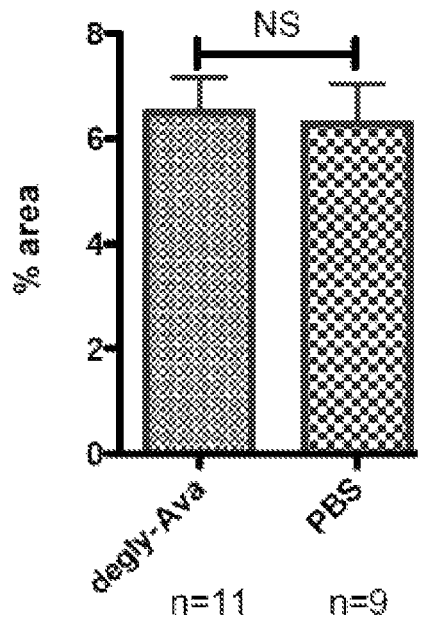
FIG. 7: Deglycosylated Avastin does not inhibit corneal neovascularization. A deglycosylated form of Avastin, which does not bind FcγRI, did not reduce corneal hemangiogenesis compared to PBS injection in wild-type mice. NS, not significant.
Figure 8:
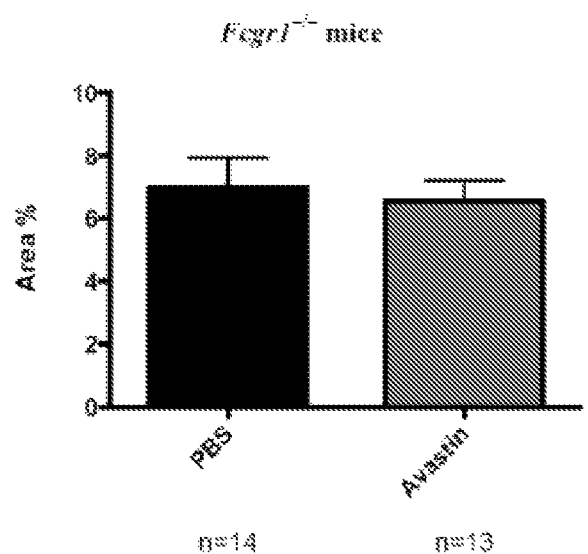
FIG. 8: Avastin does not inhibit corneal neovascularization in Fcgr1$^{-/-}$ mice. Avastin did not reduce corneal hemangiogenesis compared to PBS injection in Fcgr1$^{-/-}$ mice.

Indeed, purified human IgG1 as well as recombinant human IgG1-Fc reduced corneal hemangiogenesis in wild-type mice (FIGS. 3 and 4). The Fab and Fc fragments of bevacizumab resulting from papain enzymatic digestion were tested and it was found that bevacizumab-Fc but not bevacizumab-Fab reduced corneal hemangiogenesis in wild-type mice (FIGS. 5 and 6). Deglycosylation of human IgG1 dramatically reduces its binding to the high affinity FcγRI receptor (encoded by Fcgr1)[18,19]. It was found that deglycosylated bevacizumab did not reduce corneal hemangiogenesis in wild-type mice (FIG. 7). In addition, bevacizumab did not inhibit corneal hemangiogenesis in Fcgr1$^{-/-}$ mice (FIG. 8). Collectively, these data indicate that bevacizumab reduces mouse corneal neovascularization via FcγRI and not Vegfa inhibition.

Example 2: Bevacizumab Inhibits Mouse Choroidal Angiogenesis Via FcγRI

Figure 9:
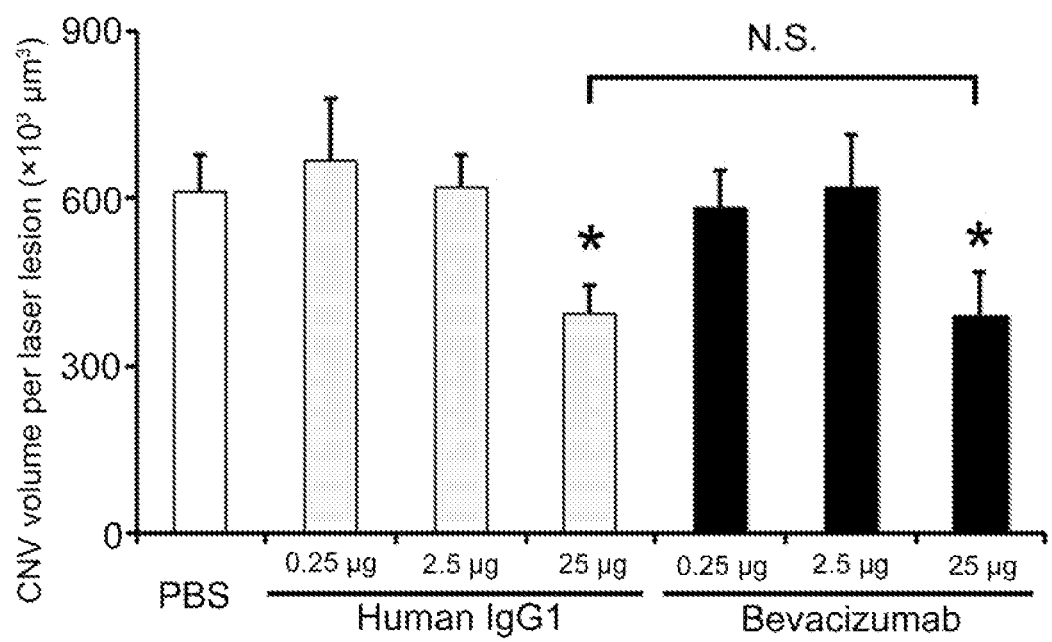
FIG. 9: Avastin and human IgG1 inhibit choroidal neovascularization. Intravitreous injection of Bevacizumab (Avastin) or human IgG1 reduced laser-induced choroidal neovascularization in wild-type mice compared to PBS. * P<0.05 compared to PBS.
Figure 10:
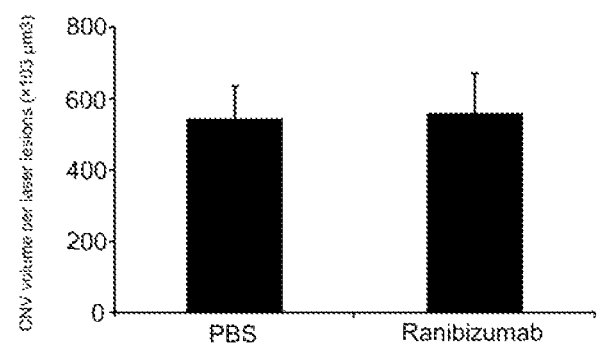
FIG. 10: Lucentis does not inhibit choroidal neovascularization. Intravitreous injection of Ranibizumab (Lucentis) did not reduce laser-induced choroidal neovascularization in wild-type mice compared to PBS. No significant difference.
Figure 11:
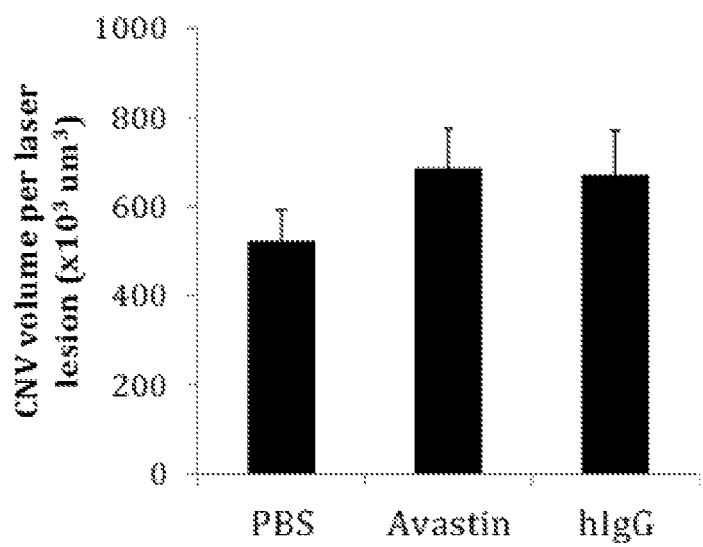
FIG. 11: Intravitreous injection of Avastin or human IgG1 did not reduce laser-induced choroidal neovascularization in Fcgr1$^{-/-}$ mice compared to PBS. No significant difference.
Figure 12:
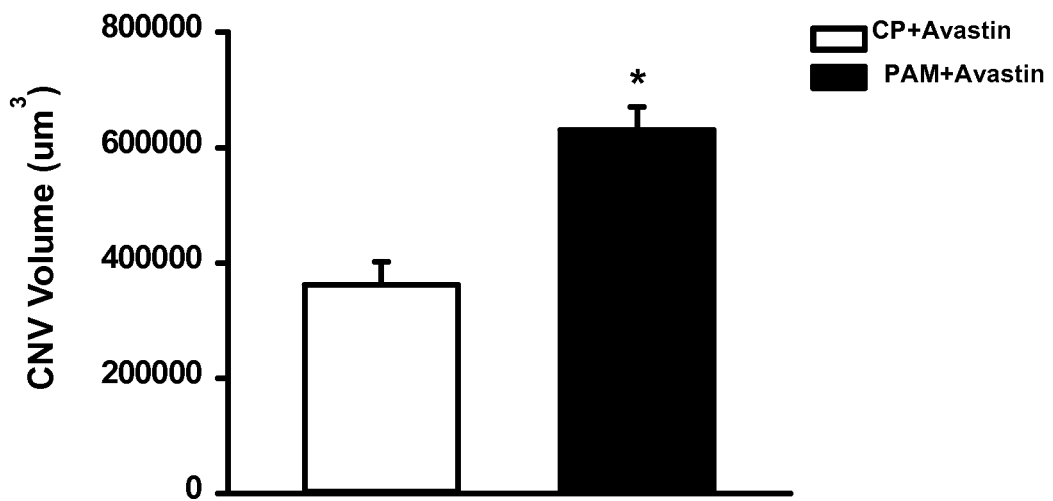
FIG. 12: Coadministration of a peptide inhibitor of IgG binding to FcγRI (PAM), compared to a control peptide (CP), blocked the inhibition of laser-induced choroidal neovascularization by Avastin in wild-type mice.

Next, a mouse model of laser injury-induced choroidal neovascularization was tested, which is a widely used model of neovascular AMD that is driven in large part by Vegfa and was predictive of the success of anti-VEGFA therapies in humans. Various drugs were administered by intravitreous injection immediately after surgery. By day 7, it was found that bevacizumab or human IgG1 but not ranibizumab inhibited choroidal neovascularization in wild-type mice compared to PBS administration (FIGS. 9 and 10). However, neither bevacizumab nor human IgG1 inhibited choroidal neovascularization in Fcgr1$^{-/-}$ mice (FIG. 11). A peptide that blocks IgG binding to FcγRI (ref.[20]), but not a control peptide, eliminated the ability of bevacizumab to inhibit choroidal neovascularization in wild-type mice (FIG. 12).

Example 3: Bevacizumab Inhibits Mouse Hind Limb Angiogenesis Via FcγRI

Figure 13:
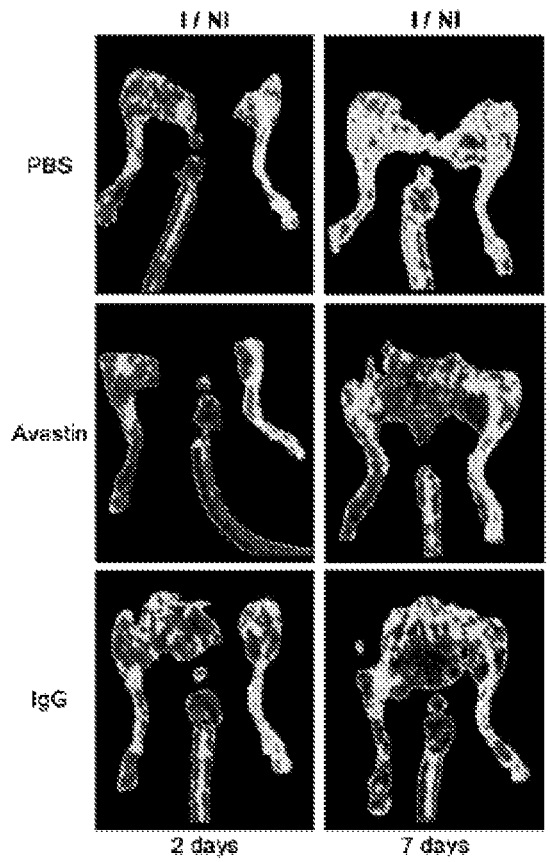
FIG. 13: (A) Color laser doppler studies were performed at 2 and 7 days after femoral artery ligation (NI, nonischemic; I, ischemic). The blue areas denote low flow/ischemic regions, whereas red denotes normal perfusion. Representative images show that whereas animals treated with intramuscular PBS demonstrate substantial reperfusion of the limb at 7 days, those treated with Avastin or human IgG injections did not.
Figure 14:
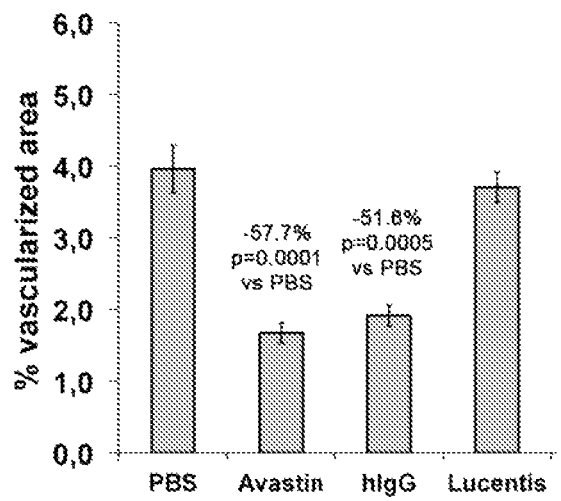
FIG. 14: Intramuscular administration of Avastin and human IgG but not Lucentis in wild-type mice reduced blood capillary density, expressed as % vascularized area normalized to myocyte numbers, compared to PBS.
Figure 15:
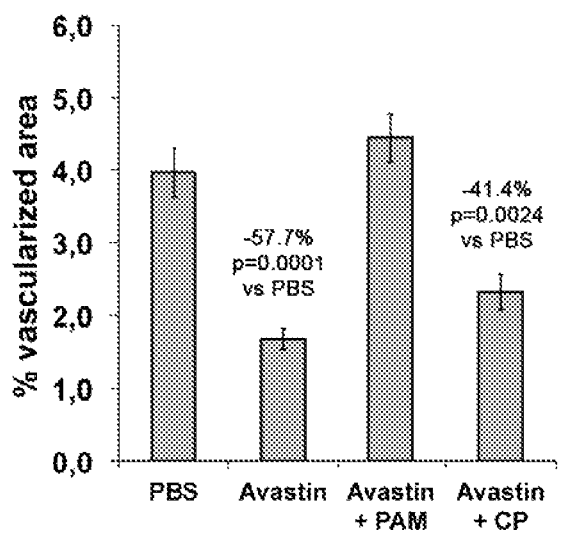
FIG. 15: Coadministration of a peptide inhibitor of IgG binding to FcγRI (PAM), compared to a control peptide (CP), blocked the inhibition of hind limb ischemia-induced neovascularization by Avastin in wild-type mice.
Figure 16:
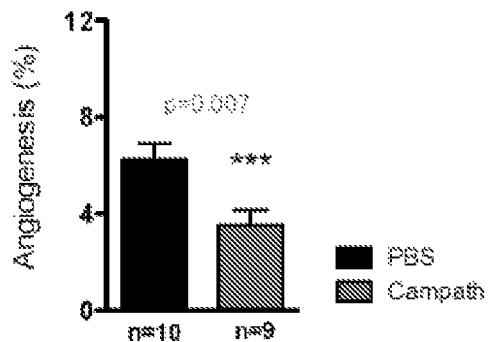
FIG. 16: Campath inhibits corneal neovascularization. Intrastromal injection of Campath (a humanized IgG1 antibody that specifically targets human CD52 but not mouse CD52; red) reduced corneal hemangiogenesis compared to PBS (black) injection in wild-type mice.
Figure 17:
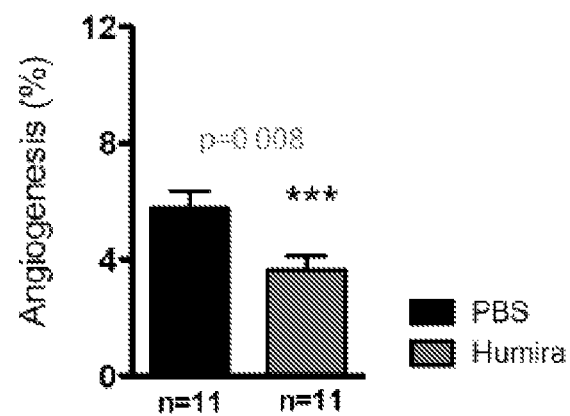
FIG. 17: Humira inhibits corneal neovascularization. Intrastromal injection of Humira (a humanized IgG1 antibody that specifically targets human TNF-α but not mouse TNF-α) reduced corneal hemangiogenesis compared to PBS injection in wild-type mice.
Figure 18:
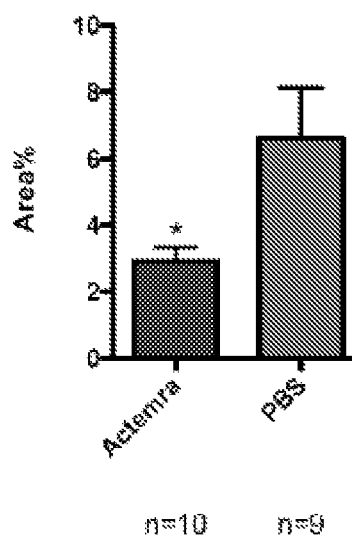
FIG. 18: Actemra inhibits corneal neovascularization. Intrastromal injection of Actemra (a humanized IgG1 antibody that specifically targets human IL-6R but not mouse IL-6R) reduced corneal hemangiogenesis compared to PBS injection in wild-type mice. * P<0.05.
Figure 19:
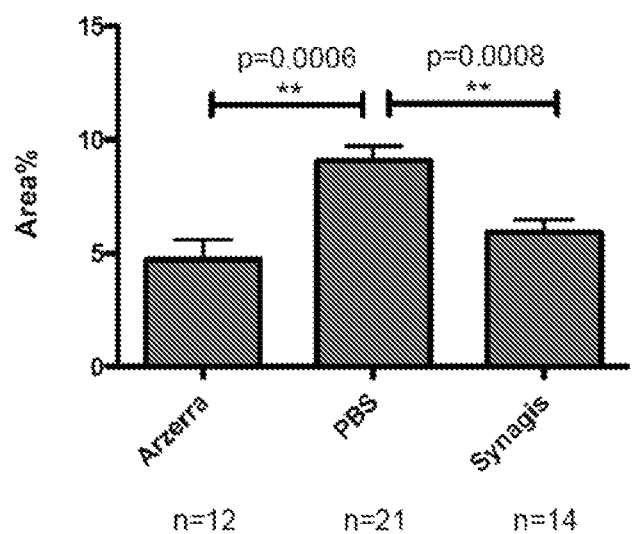
FIG. 19: Arzerra and Synagis inhibit corneal neovascularization. Intrastromal injection of Arzerra (a humanized IgG1 antibody that specifically targets human CD20 but not mouse CD20) or of Synagis (a humanized IgG1 antibody that specifically targets the F protein of respiratory syncytial virus) reduced corneal hemangiogenesis compared to PBS injection in wild-type mice. * P<0.05.
Figure 20:
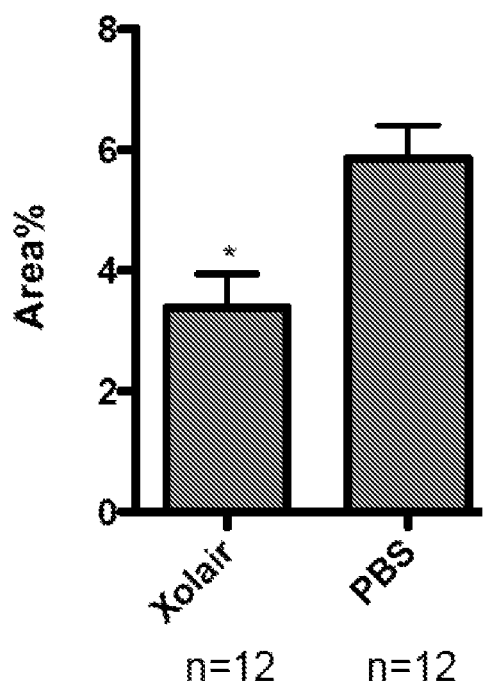
FIG. 20: Xolair inhibits corneal neovascularization. Intrastromal injection of Xolair (a humanized IgG1 antibody that specifically targets human IgE but not mouse IgE) reduced corneal hemangiogenesis compared to PBS injection in wild-type mice. * P<0.05.
Figure 21:
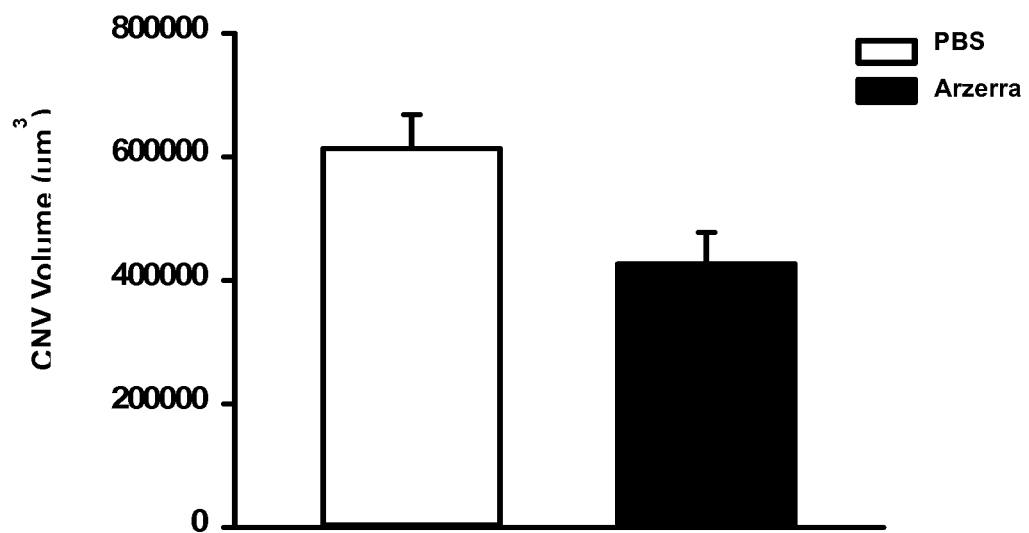
FIG. 21: Arzerra inhibits choroidal neovascularization. Intravitreous injection of atumumab (Arzerra) reduced laser-induced choroidal neovascularization in wild-type mice compared to PBS. * P<0.05 compared to PBS.
Figure 22:
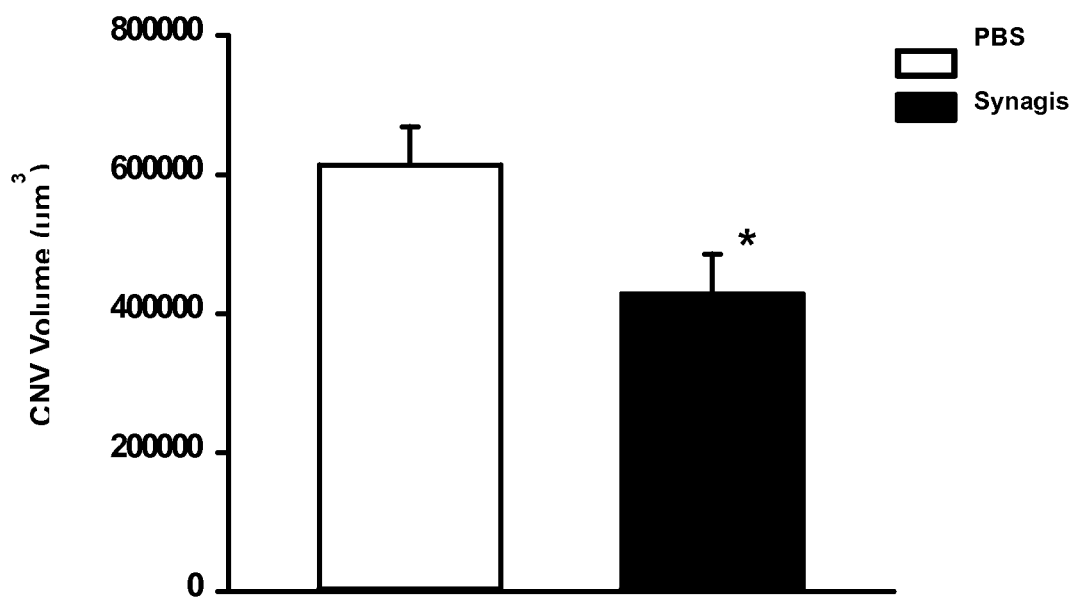
FIG. 22: Synagis inhibits choroidal neovascularization. Intravitreous injection of palivizumab (Synagis), an anti-respiratory syncytial virus protein F IgG1 antibody that does not target any mouse protein, reduced laser-induced choroidal neovascularization in wild-type mice compared to PBS. * P<0.05 compared to PBS.
Figure 23:
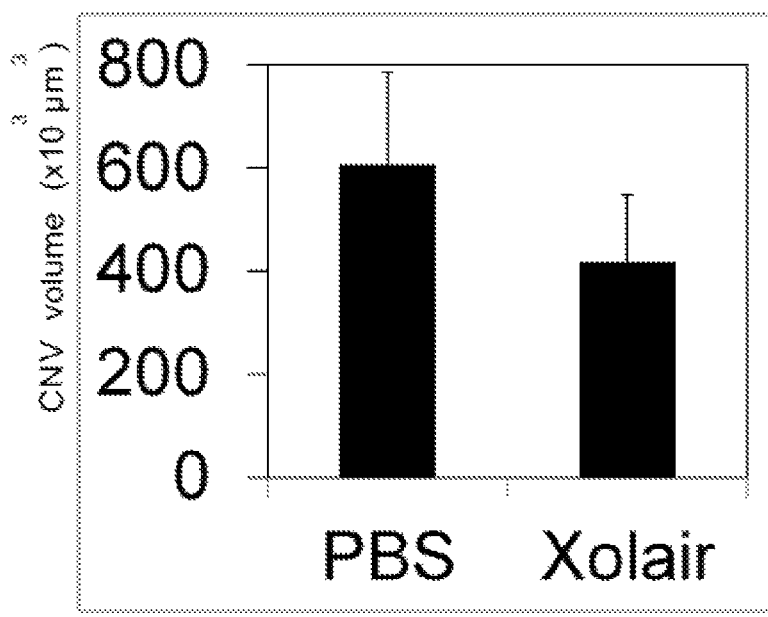
FIG. 23: Xolair inhibits choroidal neovascularization. Intravitreous injection of omalizumab (Xolair), an anti-human IgE IgG1 antibody that does not bind mouse IgE, reduced laser-induced choroidal neovascularization in wild-type mice compared to PBS. * P<0.05 compared to PBS.
Figure 24:
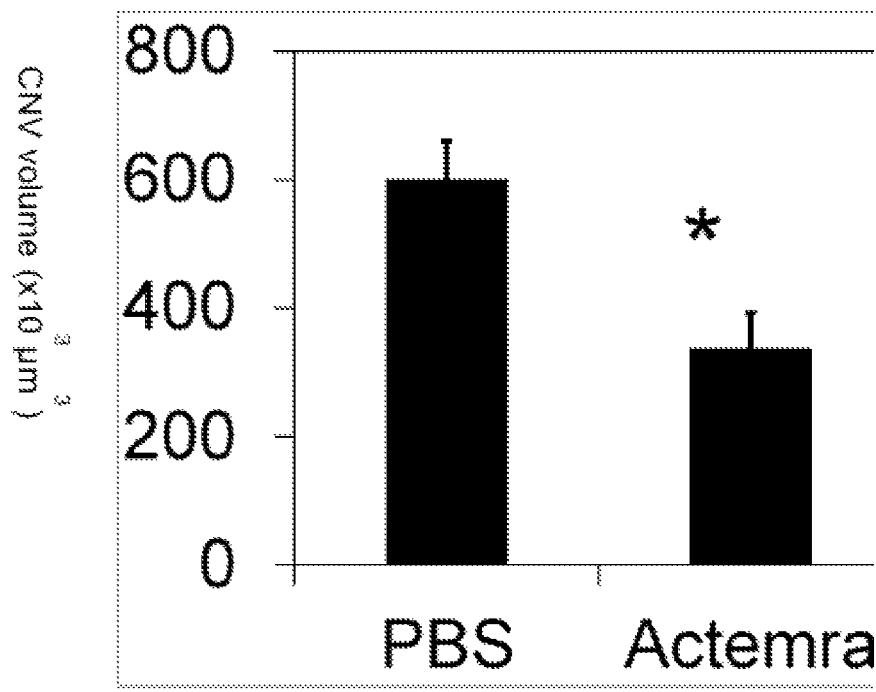
FIG. 24: Actemra inhibits choroidal neovascularization. Intravitreous injection of tocilizumab (Actemra), an anti-human IL-6R IgG1 antibody that does not bind mouse IL-6R, reduced laser-induced choroidal neovascularization in wild-type mice compared to PBS. * P<0.05 compared to PBS.
Figure 25:
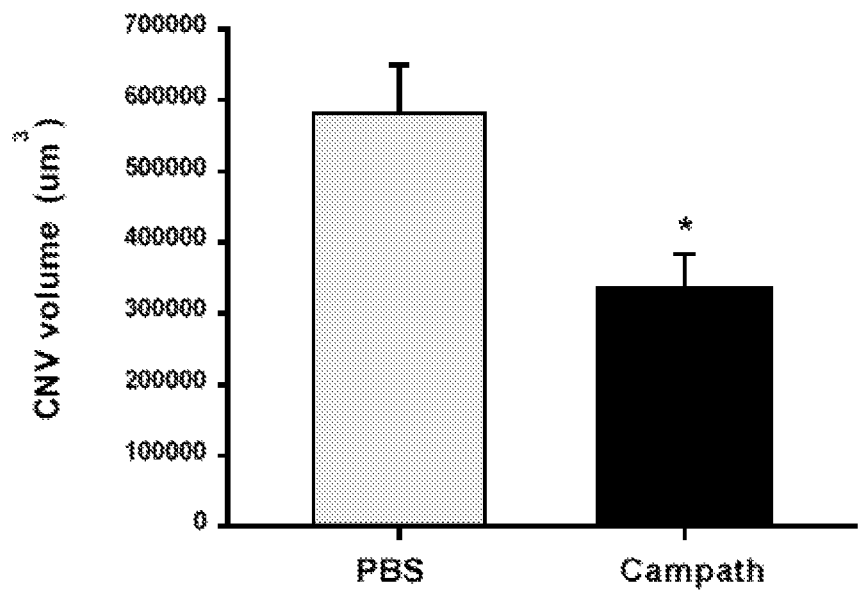
FIG. 25: Campath inhibits choroidal neovascularization. Intravitreous injection (25 μg) of alemtuzumab (Campath), an anti-human CD52 IgG1 antibody that does not bind mouse CD52, reduced laser-induced choroidal neovascularization in wild-type mice compared to PBS. * P<0.05 compared to PBS.
Figure 26:
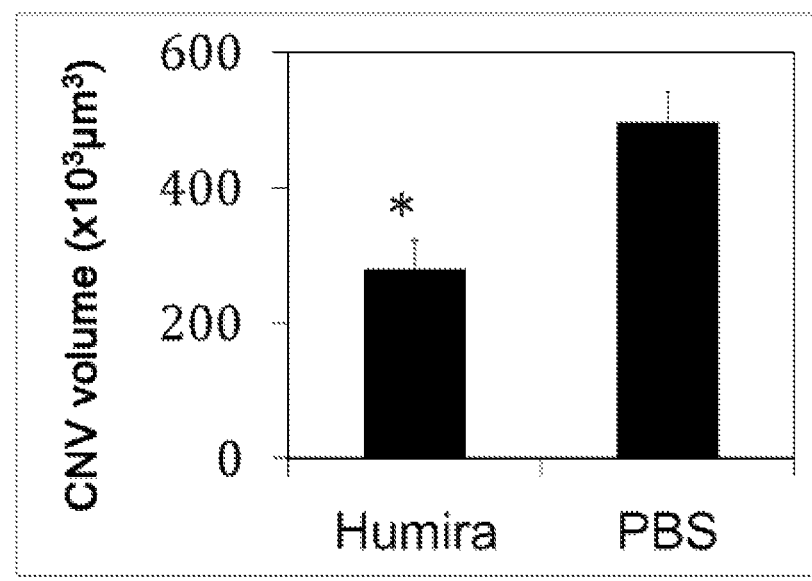
FIG. 26: Humira inhibits choroidal neovascularization. Intravitreous injection (25 μg) of adalimumab (Humira), an anti-human TNFα IgG1 antibody that does not bind mouse TNFα, reduced laser-induced choroidal neovascularization in wild-type mice compared to PBS. * P<0.05 compared to PBS.

Next, an angiogenesis model outside the eye was tested; hind limb ischemia was induced by femoral artery ligation, and drugs were administered intramuscularly at the time of surgery and 2 days thereafter. Color laser doppler imaging 2 days after ligation revealed significant reduction in blood flow in the injured limbs of all experimental groups. By day 7, PBS-injected limbs exhibited vascular rescue that was comparable to the contralateral untreated, nonischemic limb; however, limbs injected with bevacizumab or human IgG1 exhibited suppressed revascularization and diminished perfusion (FIG. 13). There was a corresponding reduction in CD31$^+$ capillary density (hemangiogenesis) in the bevacizumab-treated and human IgG1-treated limbs compared with the PBS-treated group (FIG. 14). The peptide that blocks IgG binding to FcγRI eliminated the ability of bevacizumab to inhibit hind limb neovascularization in wild-type mice (FIG. 15).

Example 4: Numerous Human IgG1s Inhibit Mouse Models of Angiogenesis Via FcγRI

Next, several human or humanized IgG1 monoclonal antibodies that are approved for treatment of various human diseases were tested—adalimumab (Humira™: anti-TNFα), alemtuzumab (Campath™: anti-CD52), ofatumumab (Arzerra™: anti-CD20), omalizumab (Xolair™: anti-IgE), tocilizumab (Actemra™: anti-IL-6R)—and that do not bind the mouse homologues of their intended human protein targets, as well as palivizumab (Synagis: anti-respiratory syncitial virus protein F), which has no mammalian target. It was found that these antibodies reduced both corneal and choroidal angiogenesis in wild-type mice (FIG. 16-26). Collectively, these data indicate that angioinhibition is a target-independent class effect of human or humanized IgG1 monoclonal antibodies that is mediated via FcγRI.

Example 5: IVIG Inhibit Mouse Models of Angiogenesis Via FcγRI

Figure 27:
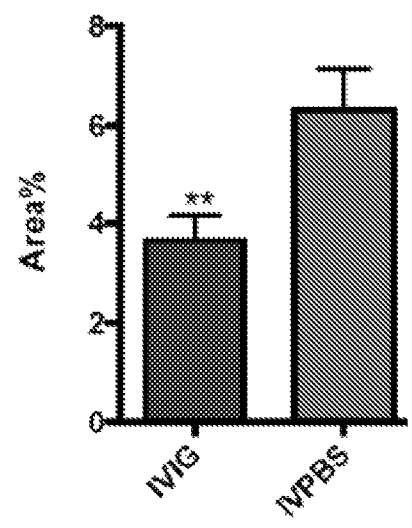
FIG. 27: IVIG inhibits corneal neovascularization. Intravenous administration of intravenous human immunoglobulin (WIG) reduced corneal hemangiogenesis compared to intravenous PBS (IVPBS) injection in wild-type mice. * P<0.05.
Figure 28:
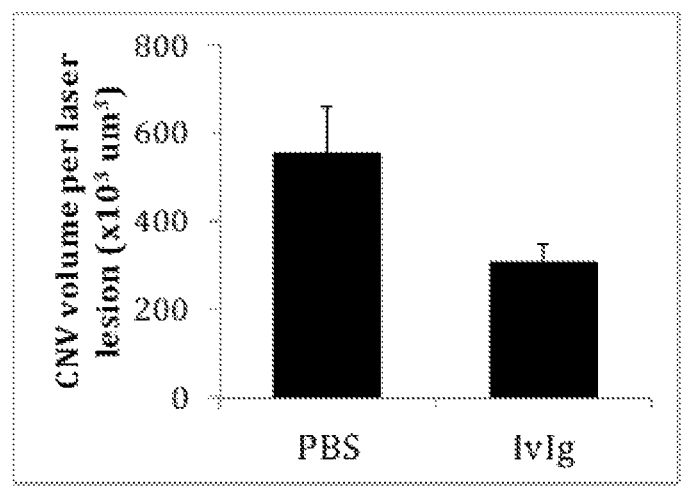
FIG. 28: IVIG inhibits choroidal neovascularization. Intravenous administration of intravenous human immunoglobulin (IvIg) reduced the volume of laser-induced choroidal neovascularization in wild-type mice.
Figure 29:
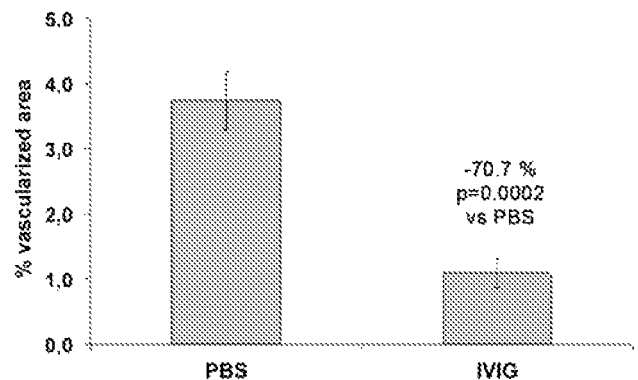
FIG. 29: IVIG inhibits hind limb neovascularization. Intravenous administration of intravenous human immunoglobulin (IvIg) reduced hind limb-induced neovascularization in wild-type mice.
Figure 30:
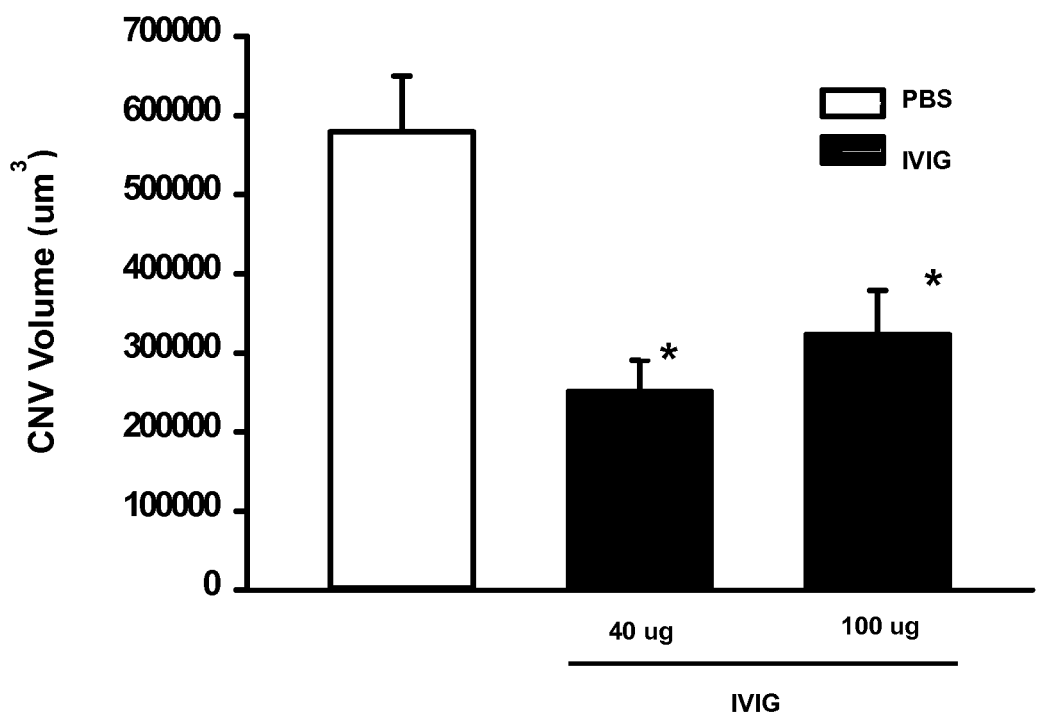
FIG. 30: Local IVIG inhibits choroidal neovascularization. Intravitreous injection of human "intravenous" immunoglobulin reduced laser-induced choroidal neovascularization in wild-type mice compared to PBS. * P<0.05 compared to PBS.

Human intravenous immunoglobulin (WIG), a purified IgG fraction obtained from the pooled plasma of thousands of donors and comprised principally of IgG1, is approved for the treatment of numerous primary immunodeficiency[24]. It is also widely used in an "off-label" fashion to treat a wide range of dermatological, neurological, inflammatory, and transplantation-related diseases and widely used to treat inflammatory diseases. It was found that intravenous administration of IVIG inhibited corneal and choroidal neovascularization in wild-type mice, compared to PBS administration (FIG. 27-29). The degree of angioinhibition was similar to that exerted by intraocular administration of various humanized IgG1 antibodies reported above. Interestingly, it was found that intravitreous administration of WIG suppressed choroidal neovascularization in wild-type mice as effectively as intravenous administration of WIG (FIG. 30). These data open the possibility of intraocular administration of IVIG as an anti-angiogenic therapy.

Example 6: mAbs Reduce Angiogenesis in FcγR Humanized Mice

Figure 31:
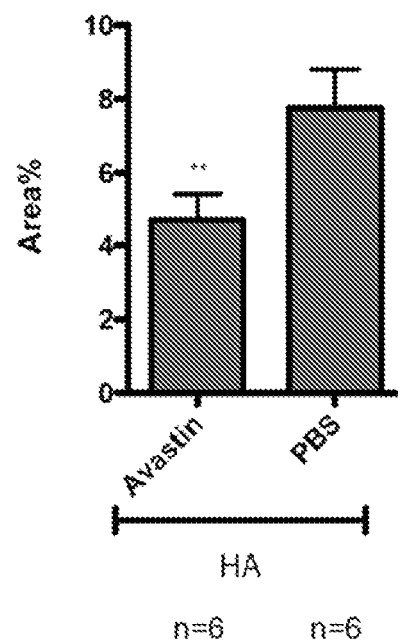
FIG. 31: Avastin inhibits corneal neovascularization in humanized FcγR mice. Intravenous administration of intravenous human immunoglobulin (IVIG) reduced corneal hemangiogenesis compared to intravenous PBS (IVPBS) injection in humanized FcγR mice compared to PBS. * P<0.05 compared to PBS.
Figure 32:
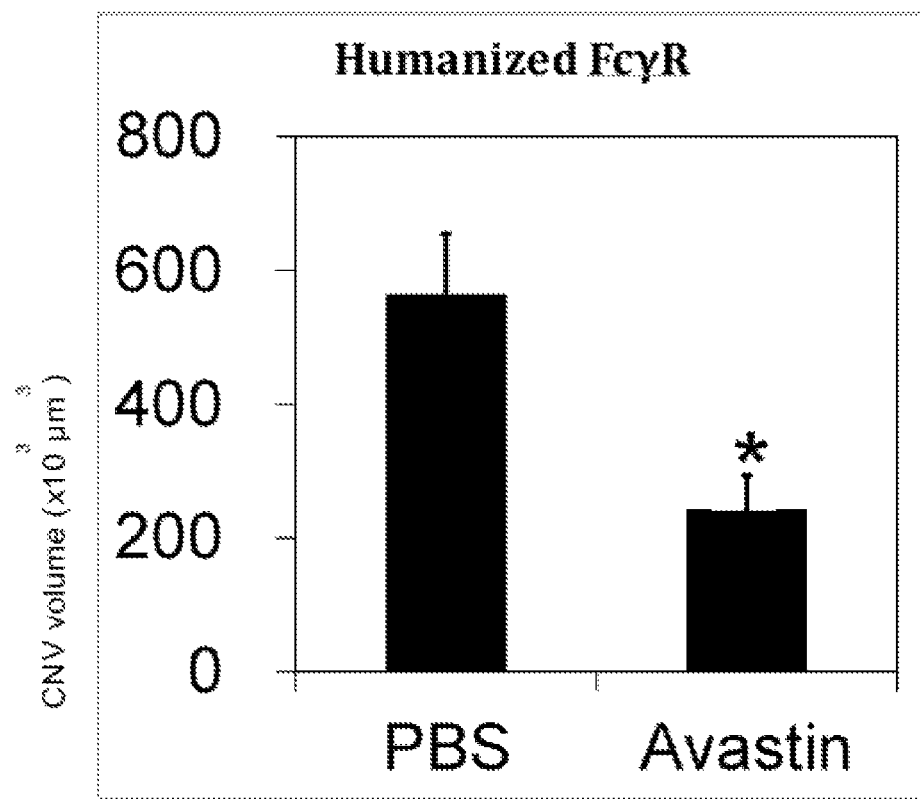
FIG. 32: Avastin inhibits choroidal neovascularization in humanized FcγR mice. Intravitreous injection of Avastin reduced laser-induced choroidal neovascularization in humanized FcγR mice compared to PBS. * P<0.05 compared to PBS.

Although human IgG1 binds and activates mouse FcγRI similarly as it does human FcγRI, the structural diversity and unique cellular expression patterns of mouse and human FcγRs are not synonymous[25]. The generation of an FcγR humanized mouse via transgenic expression of the entire human FcγR family, under the control of their human regulatory elements, on a genetic background lacking all mouse FcγRs has enabled better prediction of the functional consequences of engaging human FcγRs by IgGs (ref.[26]). In these FcγR humanized mice, it was found that bevacizumab reduced corneal and choroidal neovascularization just as in wild-type mice (FIGS. 31 and 32). These data further increase the likelihood that similar, target-independent angioinhibitory activity of humanized monoclonal IgG1 antibodies or WIG could be observed in humans.

Example 7: IgG1 mAbs Reduce Angiogenesis Via c-cbl in Macrophages

Figure 33:
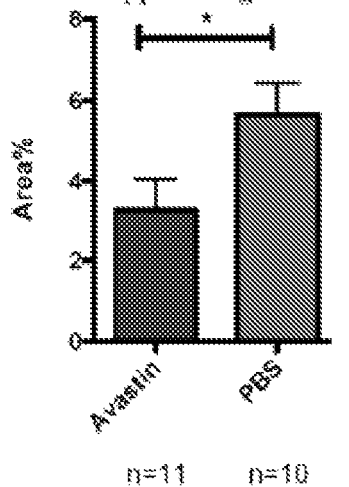
FIG. 33: FcγR1 expression on resident cells is not required for Avastin to inhibit corneal neovascularization. Avastin reduced corneal hemangiogenesis compared to PBS injection in Fcgr1$^{-/-}$ mice that had been irradiated and had their bone marrow reconstituted with wild-type mouse bone marrow. * P<0.05.
Figure 34:
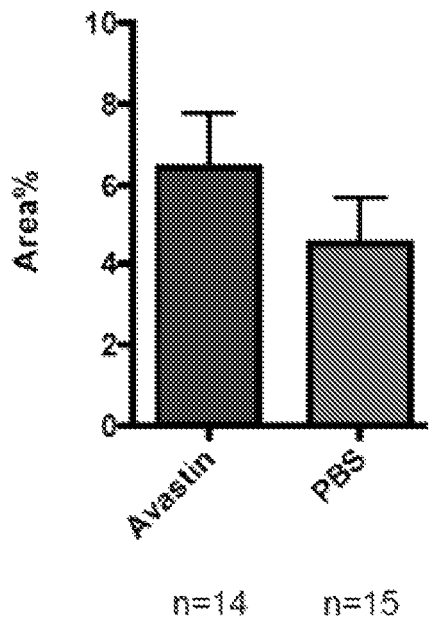
FIG. 34: FcγR1 expression on circulating cells is required for Avastin to inhibit corneal neovascularization. Avastin did not reduce corneal hemangiogenesis compared to PBS injection in wild-type mice that had been irradiated and had their bone marrow reconstituted with Fcgr1$^{-/-}$ mouse bone marrow. No significant difference.
Figure 35:
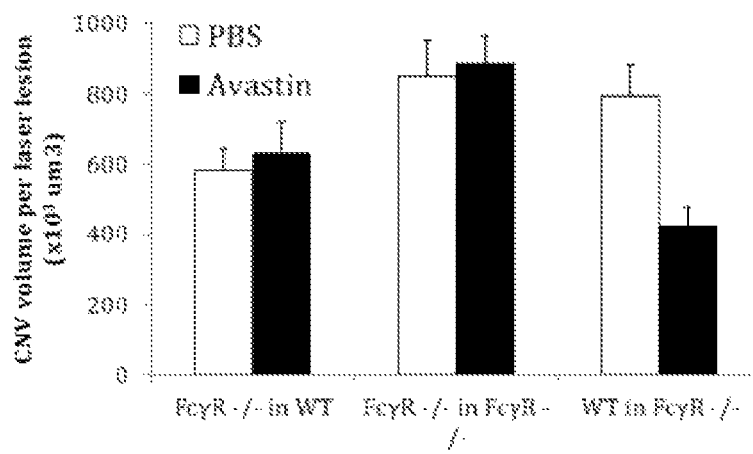
FIG. 35: FcγR1 expression on circulating cells, but not on resident cells, is required for Avastin to inhibit choroidal neovascularization. Intravitreous administration of Avastin reduced laser-induced choroidal neovascularization compared to PBS injection in Fcgr1$^{-/-}$ mice that had been irradiated and had their bone marrow reconstituted with wild-type mouse bone marrow. Avastin did not reduce laser-induced choroidal neovascularization compared to PBS injection in wild-type mice that had been irradiated and had their bone marrow reconstituted with Fcgr1$^{-/-}$ mouse bone marrow.
Figure 36:
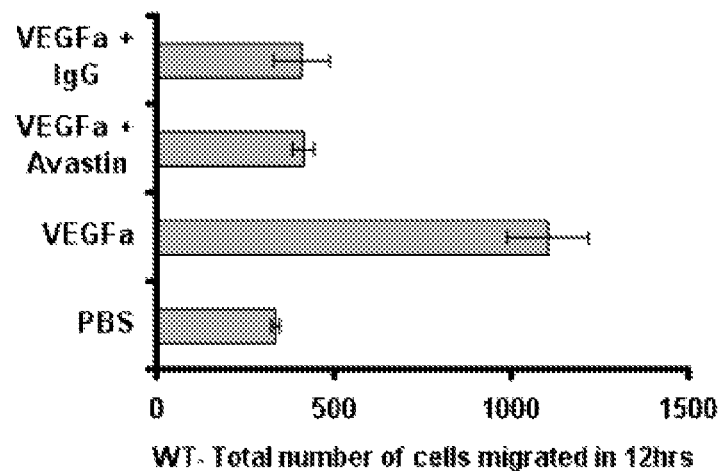
FIG. 36: Avastin and IgG inhibit mouse Vegfa-induced migration of wild-type (wt) mouse bone marrow derived macrophages across a Transwell filter.
Figure 37:
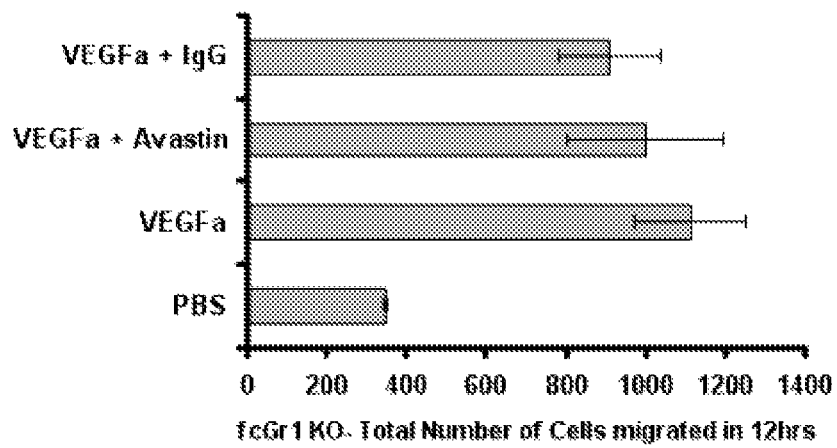
FIG. 37: Avastin and IgG do not inhibit mouse Vegfa-induced migration of Fcgr1 knockout (ko) mouse bone marrow derived macrophages across a Transwell filter.
Figure 38:
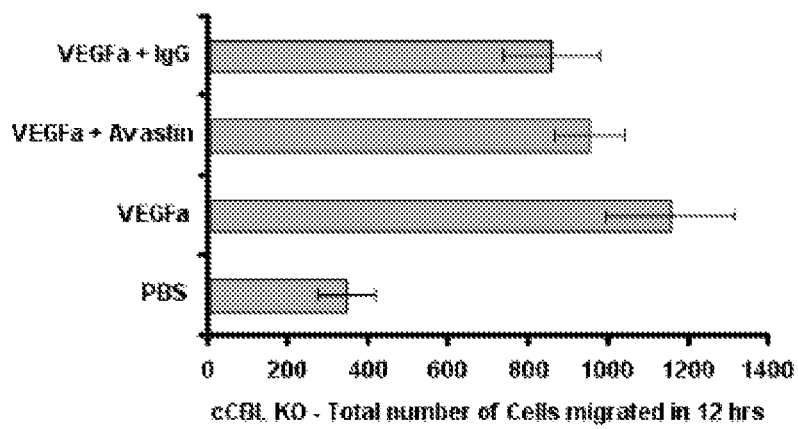
FIG. 38: Avastin and IgG do not inhibit mouse Vegfa-induced migration of c-cbl knockout (ko) mouse bone marrow derived macrophages across a Transwell filter.

To determine whether circulating or resident cell types were the critical effectors in IgG1 mAb-mediated angioinhibition, bone marrow chimeric mice were created. Bevacizumab suppressed angiogenesis in the cornea and the choroid in $Fcgr1^{-/-}$ mice receiving wild-type bone marrow but did not do so in wild-type mice receiving $Fcgr1^{-/-}$ bone marrow (FIG. 33-35). These results indicate that FcγRI expression in circulating bone marrow-derived cells is critical for bevacizumab-induced angioinhibition. The effects of humanized IgG1 mAbs on macrophages were studied because these circulating immune cells play a critical role in angiogenesis. Both bevacizumab and human IgG1 inhibited mouse Vegfa-induced migration of wild-type mouse bone marrow derived macrophages (BMDMs) but not of $Fcgr1^{-/-}$ or $c\text{-}cbr^{-/-}$ BMDMs (FIG. 36-38).

Figure 39:
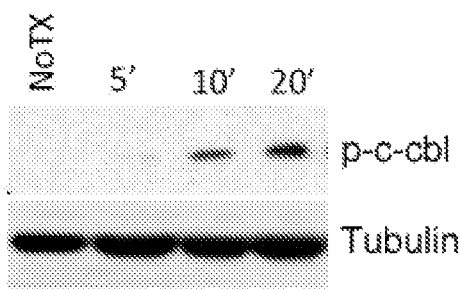
FIG. 39: Stimulation with Avastin (100 µg/ml) induced phosphorylation of c-cbl (p-c-cbl) in wild-type mouse bone marrow derived macrophages over a 20-minute period compared to no treatment (NoTx), as monitored by western blotting.
Figure 40:
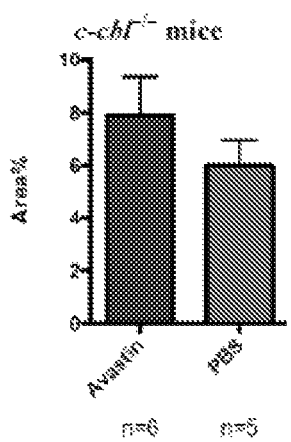
FIG. 40: c-cbl is required for Avastin to inhibit corneal neovascularization. Avastin did not reduce corneal hemangiogenesis compared to PBS injection in c-cbl$^{-/-}$ mice. No significant difference.

Bevacizumab induced phosphorylation of c-cbl (FIG. 39), a kinase that is activated by IgG1 binding to FcγRI, in wild-type mouse bone marrow derived macrophages. Bevacizumab did not inhibit corneal neovascularization in $c\text{-}cbr^{-/-}$ mice (FIG. 40), indicating that c-cbl activation is essential in this process.

Example 8: Methods

Animals.

All animal experiments were in accordance with the guidelines of the University of Kentucky Institutional Animal Care and Use Committee, and the Association for Research in Vision and Ophthalmology (ARVO) Animal Statement for the Use of Animals in Ophthalmic and Vision Research. C57Bl6/J mice were purchased from The Jackson Laboratory (Bar Harbor, Me.). For all procedures, anesthesia was performed by intraperitoneal injection of 100 mg/kg ketamine hydrochloride (Ft. Dodge Animal Health, Ft. Dodge, Iowa) and 10 mg/kg xylazine (Phoenix Scientific, St. Joseph, Mo.). Pupils were dilated with topical tropicamide (1%; Alcon Laboratories, Inc., Fort Worth, Tex.).

Choroidal Neovascularization.

Subretinal injections of antibodies (25 µg in 1 µL) in mice were performed using a Pico-Injector (PLI-100; Harvard Apparatus, Holliston, Mass.). CNV had been induced by laser photocoagulation (532 nm, 200 mW, 100 ms, 75 µm; OcuLight GL; IRIDEX Corporation, Mountain View, Calif.) performed on both eyes (4 spots per eye for volumetric analyses) of each 6- to 8-week-old male mice (N=4 per group). Seven days later CNV volumes were measured by staining with 0.5% FITC-conjugated *Griffonia simplicifolia* Isolectin B4 (Vector Laboratories, Burlingame, Calif.). RPE-choroidal flat mounts using scanning laser confocal microscope (TCS SP; Leica, Wetzlar, Germany), as reported previously. CNV volumes per laser lesion were compared by hierarchical logistic regression using repeated measures analysis.

Cornea Suture Placement.

In anesthetized animals, two interrupted 11-0 nylon sutures (Mani, Inc., Utsunomiya, Japan) were placed into the corneal stroma, midway between the central corneal apex and the limbus (approximately 1.25 mm from the limbus), of both eyes of mice. Delivery of antibodies (100 µg) or PBS was performed into corneal stroma on day 0 (immediately after suture placement), day 4, and day 8 following injection. Injections were performed using a 33-gauge Exmire Microsyringe (Ito Corporation) Animals were sacrificed at day 10, the eyes were enucleated, and the corneas were dissected for further analyses.

Corneal Flat Mounts.

After euthanasia, the corneas were isolated, washed in PBS, and fixed in 4% paraformaldehyde for 1 hour and acetone for 20 minutes at room temperature. Corneas were washed in 0.1% Tween-20 in PBS and blocked in 3% BSA in PBS for 48 hours. Incubation with rabbit anti-mouse LYVE-1 antibody (1:333; Abcam) and rat anti-mouse CD31 antibody (1:50; BD Biosciences, San Jose, Calif.) was performed for 48 hours at 4° C. The corneas were washed in 0.1% Tween-20 in PBS and incubated for 2 hours with Alexa Fluor 488 (goat anti-rabbit; 1:200; Invitrogen) and Alexa Flour 594 (goat anti-rat; 1:200; Invitrogen). Corneal flat mounts were visualized under fluorescent microscopy (Olympus, Tokyo, Japan). The images were adjusted for brightness/contrast, and converted to black and white images. Next, whole corneas were outlined using ImageJ software (NIH). Contours of lymphatic or bloodstained vessels inside the previously outlined area were optimized by threshold and converted to binary images. Area fraction (%) of neovascularized cornea was calculated compared to whole corneal surface.

Peptide Synthesis.

The tetrameric tripeptide PAM (D-Arg-D-Thr-D-Tyr)$_4$-L-Lys$_2$-L-Lys-Gly, and the scrambled control peptide (D-Thr-D-Tyr-D-Arg)$_4$-L-Lys$_2$-L-Lys-Gly, (MW 2144), were produced by solid-phase peptide synthesis by using amino acids in the D configuration. Purified peptides were dissolved at the working concentration in PBS.

Hindlimb Ischemia.

C57Bl/6J mice (N=7 per group) were anesthetized before underwent unilateral proximal femoral artery ligation. The right femoral artery was gently isolated, ligated and excised distal to the deep femoral artery and 0.5 cm proximal to the bifurcation in saphenous and popliteal arteries, as previously described (3). The non-ischemic left limb underwent a sham surgery without arterial ligation Immediately following surgery and after 48 h, Avastin (375 µg), Lucentis (300 µg), Human IgG (375 µg), PAM peptide (1 mg), Avastin plus PAM or Avastin plus Control Peptide (1 mg) were intramuscularly administered in a total volume of 30 µL to each hindlimb. The same volume of PBS was injected in control group. To evaluate the activity of commercial human intravenous immunoglobulin (IVIG), 0.5 ml (2 g/kg) of IVIG (Baxter) or PBS were delivered intravenously by tail vein injection immediately after surgery and after 72 h. 7 days later, both anterior and posterior muscles from ischemic and non-ischemic hindlimbs were harvested and processed for immunohistochemical analysis to quantify angiogenesis and lymphangiogenesis. In order to evaluate monocyte-macrophage infiltrate, C57Bl/6J mice underwent artery ligation (n=5 per group) and the treatment with IVIG. Muscles were harvested at day 2, 4 and 7 for immunohistochemical analysis.

IHC Analyses.

For mouse tissues, capillaries were stained with anti-CD31 (BD Biosciences) or anti-LYVE-1 antibodies (Abcam), monocyte-macrophages with anti-F4/80 (Serotec), and then with biotin labeled Goat anti rat secondary antibodies (Dako). For human tissues, capillaries were stained with anti-CD-31 (Dako) or anti-LYVE-1 antibodies (Abcam) and then with biotin labeled goat anti mouse secondary antibodies (Dako). Five optical fields for each sample were analyzed. Capillary number was normalized to myocyte number. Ischemic/non-ischemic ratio of vessel density or F4/80 positive area was calculated.

Color Laser Doppler Analysis.

Color laser doppler analysis were performed 2 and 7 days after femoral artery ligation using a dedicated Laser Doppler Perfusion Imaging System (LDPI, Petimed AB) with high resolution, in single mode. Hindlimbs were depilated and mice were placed on a heating plate at 37° C. The distance between the scanner head and tissue surface was 8 cm. An area of 5×5 cm was sequentially scanned and blood flow 1 mm under the surface was measured. Color-coded images were recorded, and analyses were performed calculating the average perfusion of the right and left distal limb. Dark blue color implied low or absent perfusion whereas red implied maximal perfusion.

Macrophage Migration Assay.

$2 \times 10^4$ BMDM cells were isolated from mice and suspended in 2% BMDM medium and seeded onto the upper chamber of the 8 μM polycarbonate filter (12-transwell format. The antibodies namely Avastin or IgG at concentration of 0.1 mg/ml or recombinant mouse Vegfa (50 ng/ml) were placed in the lower chamber. After 4 h of incubation the lower chambers with Avastin and IgG were respectively replaced with Avastin+mouse Vegfa and IgG+mouse Vegfa and incubated for 12 h. Macrophages that had not migrated and remained in the upper chamber were removed by gently washing the upper chamber with PBS and fixed with 4% buffered paraformaldehyde for 15 min and permeabilized with 0.025% triton-X100 for 10 min followed by staining with Hoescht (1:1000) for 30 min. The membrane inserts were washed and filers inserts were mounted using Vectashield fluorescence mounting medium. BMDM cells found on the filter, in the lower chamber, were counted as cells having undergone chemotaxis and quantified by fluorescence for cell number. Macrophages were quantified for total number of cells migrated from the entire 32 mm diameter membrane (20× magnification of montage images) acquired using Cell Dimension Software. Cell numbers were acquired using NIH-Image J and the experiment for each condition was performed in triplicate.

Receptor Phosphorylation and Western Blotting.

Py4 mouse blood endothelial cells were starved for 16 hours in absence of FBS. To induce VEGFR-2 activation, cells were stimulated with 50 ng/ml of mVegf-A or hVEGF-A for 10 minutes. 0.1 mg/ml Avastin (Genentech) was added to medium at the same time. As a control, 0.75 μg/ml neutralizing anti-mouse Vegf-A mAb (R&D Systems) was used. To activate c-cbl phosphorylation, J774 mouse macrophages were starved for 4 h in absence of FBS and then stimulated with 0.1 mg/ml of Avastin (Genentech) or human IgG (Sigma-Aldrich) for 45 min. Cells lysed in RIPA lysis buffer (Sigma-Aldrich) supplemented protease cocktail inhibitor were homogenized by sonication. Equal amounts of protein samples (20-40n) prepared in Laemmli buffer were resolved by SDS-PAGE on Novex® Tris-Glycine Gels (Invitrogen), and transferred onto Immun-Blot PVDF membranes (Bio-Rad). The transferred membranes were blocked for 1 hr at RT and incubated with antibodies against phospho-VEGFR2 (1:1000; Cell Signaling) or phospho-c-Cbl (1:1000; Cell Signaling), at 4'C overnight. The immunoreactive bands were developed by enhanced chemiluminescence reaction. Protein loading was assessed by western blotting using an anti-Tubulin antibody (1:1000; Sigma-Aldrich).

Avastin Deglycosylation.

To deglycosylate Avastin, it was treated with PNGaseF (New England BioLab, Beverly, Mass.). Briefly, the Avastin were first denatured at 100° C. for 10 min in glycoprotein denaturing buffer and then chilled on ice. Following addition of G7 reaction buffer, the deglycosylation enzyme cocktail was added and incubated reaction at 37° C. for 4 hours. Either mock-treated or deglycosylated Avastin were subjected to SDS-PAGE and Coomassie to appreciate the mobility shift following the glycosylation procedure.

Avastin Fab/Fc Fragmentation.

Avastin Fc and Fab fragments were prepared by using a ImmunoPure Fab Preparation Kit (Thermo Fisher Scientific) according to the manufacturer's instructions. In brief, 4 mg of Avastin was mixed with 0.5 ml of immobilized papain. The mixture was incubated by shaking overnight at 37° C. Crude digest was separated from immobilized papain and applied to a protein A column (AffinityPak; Thermo Fisher Scientific). Fab fragments were recovered in the flow through. Fc fragments and undigested IgG bound to the column were eluted with elution buffer. The fragmentation was confirmed in a reducing 4-12% NuPAGE gels stained with SimplyBlue SafeStain (Invitrogen Corp.). The more clear Fab and Fc fraction were chosen and concentrated using a Vivaspin 20 centrifugal concentrator (10-kDa molecular weight cutoff; Sartorius Stedim Biotech).

Statistical Analysis.

Data are expressed as mean±SEM, with $P<0.05$ considered statistically significant. Differences among groups were tested by one-way ANOVA. Tukey HD test was used as a post hoc test to identify which group differences account for the significant overall ANOVA. All calculations were carried out using SPSS statistical package (vers 12.1; SPSS, Inc., Chicago, Ill.).

Throughout this document, various references are mentioned. All such references are incorporated herein by reference, including the references set forth in the following list:

REFERENCES

1. Nelson, A. L., Dhimolea, E. & Reichert, J. M. Development trends for human monoclonal antibody therapeutics. *Nat Rev Drug Discov* 9, 767-774 (2010).
2. Presta, L. G. et al. Humanization of an anti-vascular endothelial growth factor monoclonal antibody for the therapy of solid tumors and other disorders. *Cancer Res* 57, 4593-4599 (1997).
3. Ferrara, N., Hillan, K. J., Gerber, H. P. & Novotny, W. Discovery and development of bevacizumab, an anti-VEGF antibody for treating cancer. *Nat Rev Drug Discov* 3, 391-400 (2004).
4. Martin, D. F. et al. Ranibizumab and bevacizumab for neovascular age-related macular degeneration. *N Engl J Med* 364, 1897-1908 (2011).

5. Yu, L. et al. Interaction between bevacizumab and murine VEGF-A: a reassessment. *Invest Ophthalmol Vis Sci* 49, 522-527 (2008).
6. Gerber, H. P. et al. Mice expressing a humanized form of VEGF-A may provide insights into the safety and efficacy of anti-VEGF antibodies. *Proc Natl Acad Sci USA* 104, 3478-3483 (2007).
7. Liang, W. C. et al. Cross-species vascular endothelial growth factor (VEGF)-blocking antibodies completely inhibit the growth of human tumor xenografts and measure the contribution of stromal VEGF. *J Biol Chem* 281, 951-961 (2006).
8. Dastjerdi, M. H. et al. Effects of topical and subconjunctival bevacizumab in high-risk corneal transplant survival. *Invest Ophthalmol Vis Sci* 51, 2411-2417 (2010).
9. Rabinowitz, R., Friel, A., Rosner, M., Pri-Chen, S. & Spierer, A. Avastin treatment reduces retinal neovascularization in a mouse model of retinopathy of prematurity. *Curr Eye Res* 37, 624-629 (2012).
10. Manzano, R. P. et al. Inhibition of experimental corneal neovascularisation by bevacizumab (Avastin). *Br J Ophthalmol* 91, 804-807 (2007).
11. Hashemian, M. N., Moghimi, S., Kiumehr, S., Riazi, M. & Amoli, F. A. Prevention and treatment of corneal neovascularization: comparison of different doses of subconjunctival bevacizumab with corticosteroid in experimental rats. *Ophthalmic Res* 42, 90-95 (2009).
12. Avisar, I., Weinberger, D. & Kremer, I. Effect of subconjunctival and intraocular bevacizumab injections on corneal neovascularization in a mouse model. *Curr Eye Res* 35, 108-115 (2010).
13. Dratviman-Storobinsky, O., Lubin, B. C., Hasanreisoglu, M. & Goldenberg-Cohen, N. Effect of subconjunctival and intraocular bevacizumab injection on angiogenic gene expression levels in a mouse model of corneal neovascularization. *Mol Vis* 15, 2326-2338 (2009).
14. Akkoyun, I. et al. Structural consequences after intravitreal bevacizumab injection without increasing apoptotic cell death in a retinopathy of prematurity mouse model. *Acta Ophthalmol* 90, 564-570 (2012).
15. Ravetch, J. V. & Kinet, J. P. Fc receptors. *Annu Rev Immunol* 9, 457-492 (1991).
16. Albuquerque, R. J. et al. Alternatively spliced vascular endothelial growth factor receptor-2 is an essential endogenous inhibitor of lymphatic vessel growth. *Nat Med* 15, 1023-1030 (2009).
17. Chen, Y. et al. Selection and analysis of an optimized anti-VEGF antibody: crystal structure of an affinity-matured Fab in complex with antigen. *J Mol Biol* 293, 865-881 (1999).
18. Tao, M. H. & Morrison, S. L. Studies of aglycosylated chimeric mouse-human IgG. Role of carbohydrate in the structure and effector functions mediated by the human IgG constant region. *J Immunol* 143, 2595-2601 (1989).
19. Walker, M. R., Lund, J., Thompson, K. M. & Jefferis, R. Aglycosylation of human IgG1 and IgG3 monoclonal antibodies can eliminate recognition by human cells expressing Fc gamma RI and/or Fc gamma RH receptors. *Biochem J* 259, 347-353 (1989).
20. Marino, M., Ruvo, M., De Falco, S. & Fassina, G. Prevention of systemic lupus erythematosus in MRL/lpr mice by administration of an immunoglobulin-binding peptide. *Nat Biotechnol* 18, 735-739 (2000).
21. Takeda, A. et al. CCR3 is a target for age-related macular degeneration diagnosis and therapy. *Nature* 460, 225-230 (2009).
22. Nishijima, K. et al. Vascular endothelial growth factor-A is a survival factor for retinal neurons and a critical neuroprotectant during the adaptive response to ischemic injury. *Am J Pathol* 171, 53-67 (2007).
23. Saint-Geniez, M. et al. Endogenous VEGF is required for visual function: evidence for a survival role on muller cells and photoreceptors. *PLoS One* 3, e3554 (2008).
24. Gelfand, E. W. Intravenous immune globulin in autoimmune and inflammatory diseases. *N Engl J Med* 367, 2015-2025 (2012).
25. Rogers, K. A., Scinicariello, F. & Attanasio, R. IgG Fc receptor III homologues in nonhuman primate species: genetic characterization and ligand interactions. *J Immunol* 177, 3848-3856 (2006).
26. Smith, P., DiLillo, D. J., Bournazos, S., Li, F. & Ravetch, J. V. Mouse model recapitulating human Fcgamma receptor structural and functional diversity. *Proc Natl Acad Sci USA* 109, 6181-6186 (2012).

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of suppressing angiogenesis, comprising: intravitreously administering to a subject in need of treatment for a condition associated with angiogenesis an isolated Fc fragment of an IgG1 antibody, wherein the administered Fc fragment decreases new blood vessel formation.

2. The method of claim 1, and further comprising administering a drug selected from the group consisting of: bevacizumab, ranibizumab, trastuzumab, sorafenib (Nexavar), sunitinib (Sutent), pazopanib (Votrient), everolimus (Afinitor).

3. The method of claim 1, wherein the antibody is monoclonal.

4. The method of claim 1, wherein the antibody is humanized.

5. The method of claim 1, further comprising administering an additional therapeutic agent.

6. The method of claim 5, wherein the additional therapeutic agent is an angiogenesis-inhibiting compound.

7. The method of claim 5, wherein the additional therapeutic agent is an anticancer compound.

8. The method of claim 1, wherein the subject is a human.

9. The method of claim 1, wherein the IgG1 antibody is not selected from the group consisting of bevacizumab, trastuzumab, ado-trastuzumab emtansine, adalimumab, golimumab, efalizumab, canakinumab, pertuzumab, and intravenous immunoglobulin; or is selected from the group consisting of tocilizumab, atilizumab, ofatumumab, alemtuzumab, palivizumab, motavizumab, raxibacumab, belimumab, omalizumab, ipilmumab, daclizumab, ustekinumab, alefacept, elotuzumab, ACE-011, ACE-031, MGAWN1, NCT01736683, MNRP1685A, IMC-A12, IMC 1121B, FG-3019, MT203, necitumumab, immunex, hLL1, IMGN388, AMG 479, AIN457, CD4-IgG, J695, BIIB023, AIN457, IMC-1121B, MEDI4893, nimotuzumab, mepolizumab, TRC105, solanezumab, and ficlatuzumab.

* * * * *